(12) United States Patent
Kristiansen et al.

(10) Patent No.: US 8,593,636 B2
(45) Date of Patent: Nov. 26, 2013

(54) PIPE SYSTEM, A FLUID SENSING SYSTEM FOR A PIPE SYSTEM, AND A METHOD OF DETERMINING A FLUID COMPONENT IN AN ANNULUS CAVITY OF A PIPE

(75) Inventors: Mikael Kristiansen, Hellerup (DK); Nicky Weppenaar, Kobenhavn K (DK)

(73) Assignee: National Oilwell Varco Denmark I/S, Brondby (DK)

( * ) Notice: Subject to any disclaimer, the term of this patent is extended or adjusted under 35 U.S.C. 154(b) by 551 days.

(21) Appl. No.: 12/919,070

(22) PCT Filed: Feb. 23, 2009

(86) PCT No.: PCT/DK2009/000050
§ 371 (c)(1),
(2), (4) Date: Oct. 19, 2010

(87) PCT Pub. No.: WO2009/106078
PCT Pub. Date: Sep. 3, 2009

(65) Prior Publication Data
US 2011/0026031 A1    Feb. 3, 2011

(30) Foreign Application Priority Data

Feb. 25, 2008  (DK) .......................... PA 2008 00263
Jun. 3, 2008   (DK) .......................... PA 2008 00766

(51) Int. Cl.
*G01N 21/00* (2006.01)

(52) U.S. Cl.
USPC ....... 356/436; 73/24.02; 73/64.48; 73/152.18

(58) Field of Classification Search
USPC ........ 73/24.01, 24.02, 61.48, 152.18, 152.19; 356/436, 437
See application file for complete search history.

(56) References Cited

U.S. PATENT DOCUMENTS

| | | | |
|---|---|---|---|
| 4,270,049 A | 5/1981 | Tanaka et al. | |
| 4,450,711 A | 5/1984 | Claude | |

(Continued)

FOREIGN PATENT DOCUMENTS

| | | |
|---|---|---|
| DK | PA 2006 01706 A | 12/2006 |
| DK | PA 2007 01203 A | 8/2007 |

(Continued)

OTHER PUBLICATIONS

International Search Report for PCT/DK2009/000050 dated Jun. 22, 2009.

(Continued)

*Primary Examiner* — Hezron E Williams
*Assistant Examiner* — Nathaniel Kolb
(74) *Attorney, Agent, or Firm* — Pearne & Gordon LLP

(57) ABSTRACT

The invention relates to a pipe system comprising
a) a pipe,
b) a fluid sensing station and
c) a remote light detector system.

The pipe comprises a flow channel and an annular fluid cavity surrounding the flow channel. The fluid sensing station comprises a sensing fluid cavity which is in fluid communication with the annular fluid cavity, and the sensing fluid cavity comprises a light emitter and a light receiver placed at a distance from each other. The light emitter and the light receiver are optically connected to each other and optically connected to the remote light detector system.

The invention also relates to a fluid sensing system for sensing a fluid in an annulus cavity of a pipe, said fluid sensing system comprises a fluid sensing station and a remote light detector system. The fluid sensing station comprises a sensing fluid cavity comprising a light emitter and a light receiver placed at a distance from each other and optically connected to each other. The remote light detector system comprises a light source and an analyzer. The light emitter is optically connected to the light source, and the light receiver being optically connected to the analyzer. The fluid sensing station is arranged to be connected to a pipe with an annular fluid cavity to provide a fluid communication between said annular fluid cavity and said sensing fluid cavity.

The invention further relates to a method for sensing a fluid in an annulus cavity of a pipe.

41 Claims, 14 Drawing Sheets

(56) References Cited

U.S. PATENT DOCUMENTS

| | | | |
|---|---|---|---|
| 4,749,855 A | 6/1988 | Watanabe | |
| 4,790,652 A | 12/1988 | Uneus et al. | |
| 5,090,871 A | 2/1992 | Story et al. | |
| 5,125,749 A * | 6/1992 | Leugers et al. | 356/432 |
| 6,361,299 B1 | 3/2002 | Quigley et al. | |
| 6,412,825 B1 | 7/2002 | Langkjaer | |
| 6,706,348 B2 * | 3/2004 | Quigley et al. | 428/36.3 |
| 6,923,477 B2 | 8/2005 | Buon et al. | |
| 7,024,941 B2 | 4/2006 | Andersen | |
| 7,245,380 B2 | 7/2007 | Kosterev | |
| 7,296,480 B2 | 11/2007 | De Aquino | |
| 2002/0109080 A1* | 8/2002 | Tubel et al. | 250/227.14 |
| 2004/0177891 A1 | 9/2004 | Spaolonzi et al. | |
| 2005/0232703 A1* | 10/2005 | Saint-Marcoux | 405/154.1 |
| 2006/0027021 A1* | 2/2006 | Choi et al. | 73/579 |
| 2006/0266108 A1* | 11/2006 | DiFoggio | 73/152.47 |
| 2011/0153225 A1* | 6/2011 | Mangal et al. | 702/24 |

FOREIGN PATENT DOCUMENTS

| | | |
|---|---|---|
| GB | 2062877 A | 5/1981 |
| JP | 54079695 A | 6/1979 |
| JP | 60159625 A | 8/1985 |
| JP | 09288058 A | 11/1997 |
| WO | 03/056313 A1 | 7/2003 |
| WO | 2004/085905 A1 | 10/2004 |
| WO | 2008/077410 A1 | 7/2008 |

OTHER PUBLICATIONS

Written Opinion for PCT/DK2009/000050 dated Jun. 22, 2009.

"Recommended Practice for Flexible Pipe," API Recommended Practice 17B, Third Edition, API Publishing Services, Washington, D.C., Mar. 1, 2002.

"Specification for Unbonded Flexible Pipe," API Specification 17J, Second Edition, API Publishing Services, Nov. 1, 1999.

Kosterev, et al., "Ultrasensitive Gas Detection by Quartz-Enhanced Photoacoustic Spectroscopy in the Fundamental Molecular Absorption Bands Region," Appl. Phys. B 80, pp. 133-138, 2005.

Ngai, et al., "Continuous Wave Optical Parametric Oscillator for Quartz-Enhanced Photoacoustic Trace Gas Sensing," Appl. Phys. B 89, pp. 123-128, 2007.

Filus, et al., "A Novel Apparatus Based on a Photoacoustic Gas Detection System for Measuring Permeation Parameters of Polymer Samples," Polymer Testing, Elsevier, vol. 26, No. 5, Jun. 28, 2007, pp. 606-613.

Kosterev, et al., "Multi-Species QEPAS Based Gas Sensing Using a Wavelength-Programmable Diode Laser Source," 2002.

Lewicki, et al. "QEPAS Based Detection of Broadband Absorbing Molecules Using a Widely Tunable, CW Quantum Cascade Laser at 8.4 μm," 2007 Optical Society of America, Jun. 11, 2007, vol. 15, No. 12, Optics Express 7359-7366.

* cited by examiner

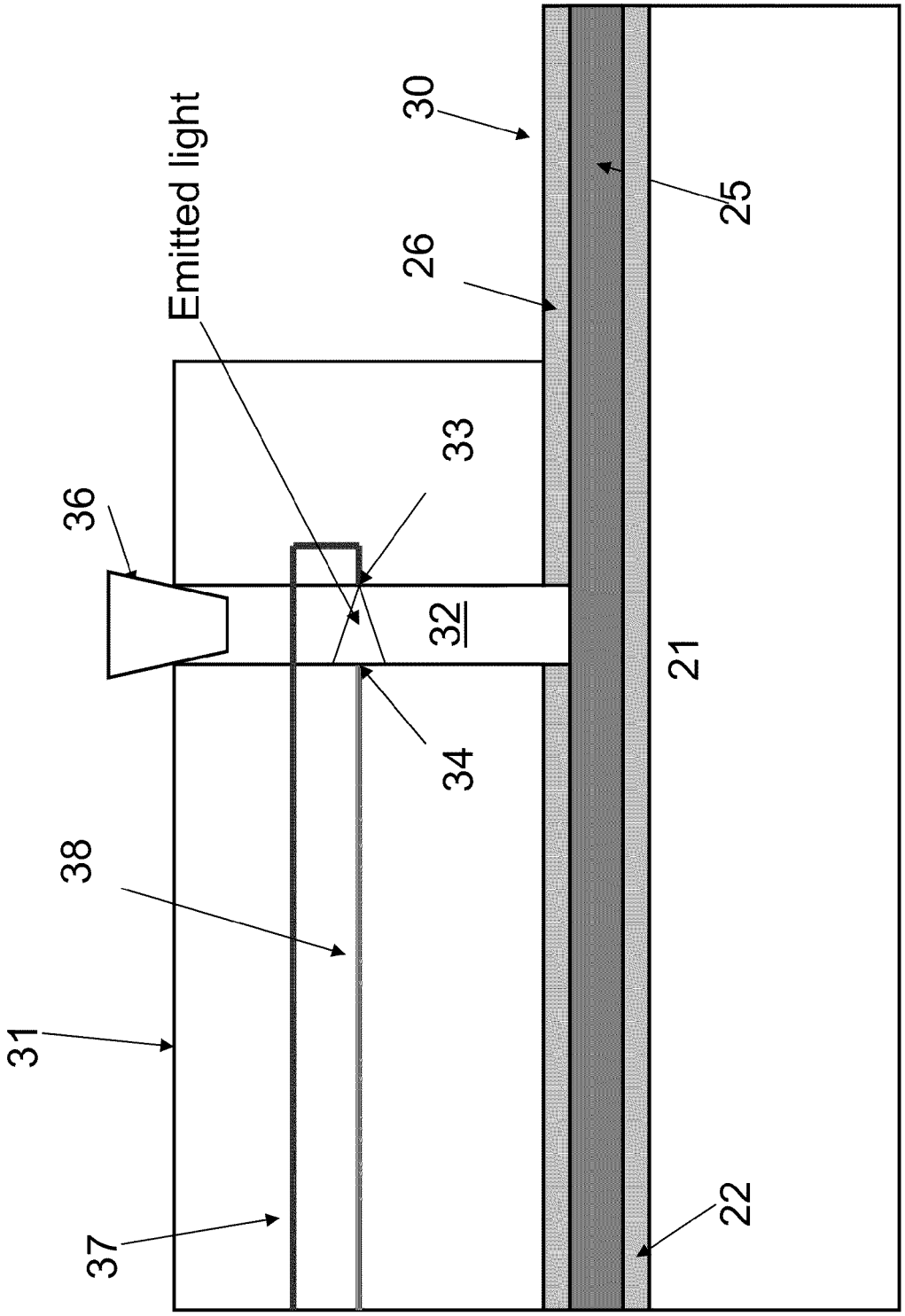

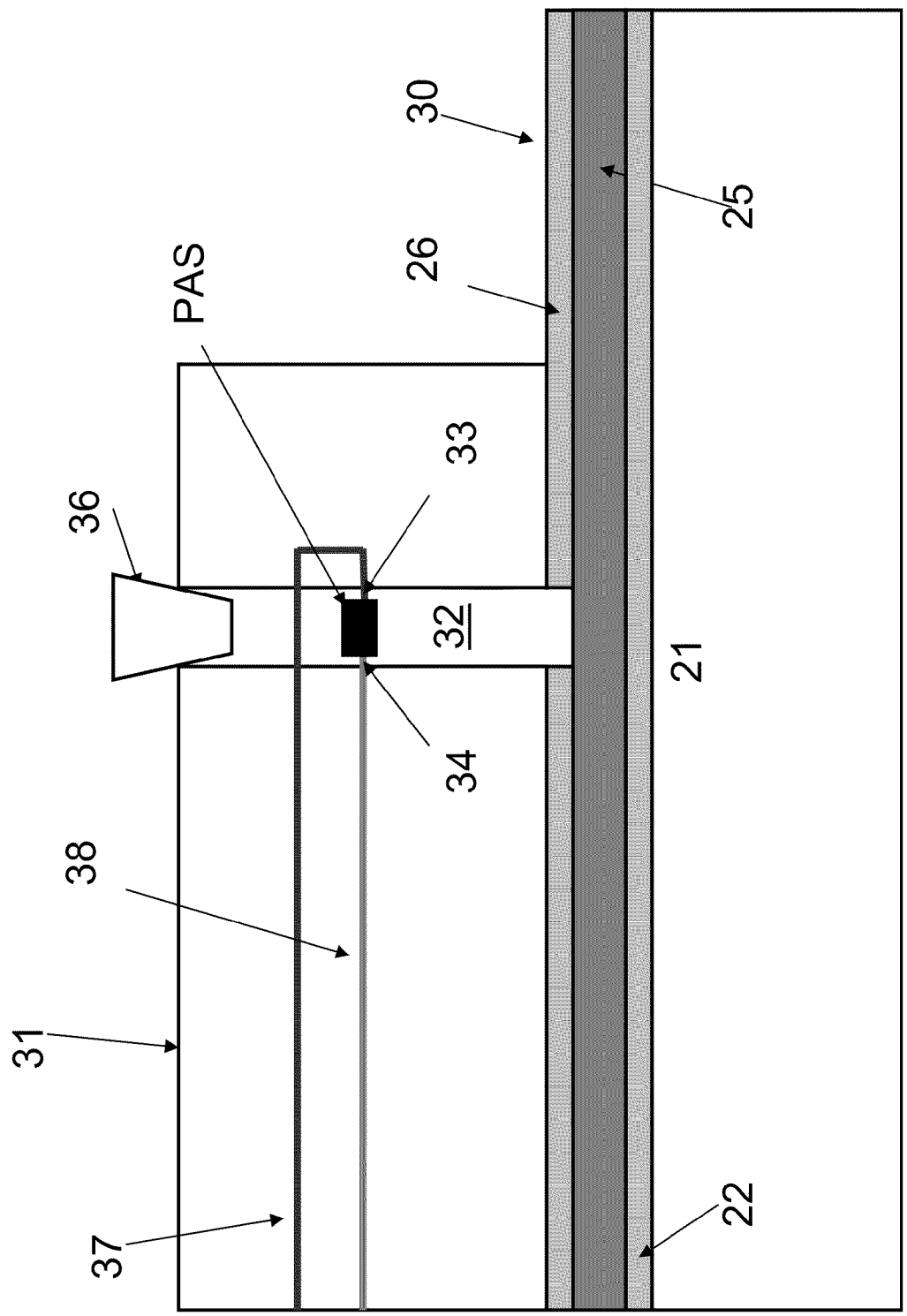

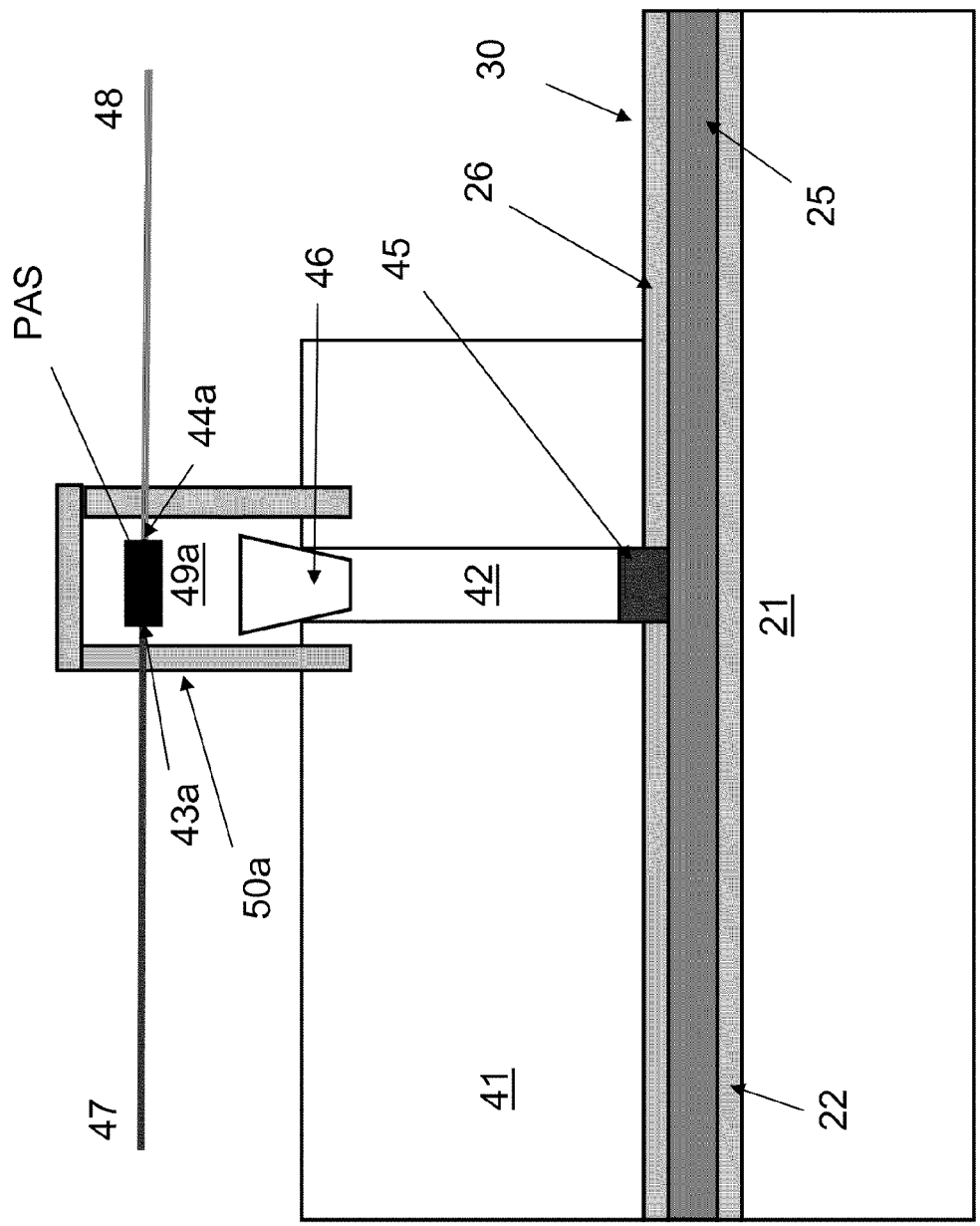

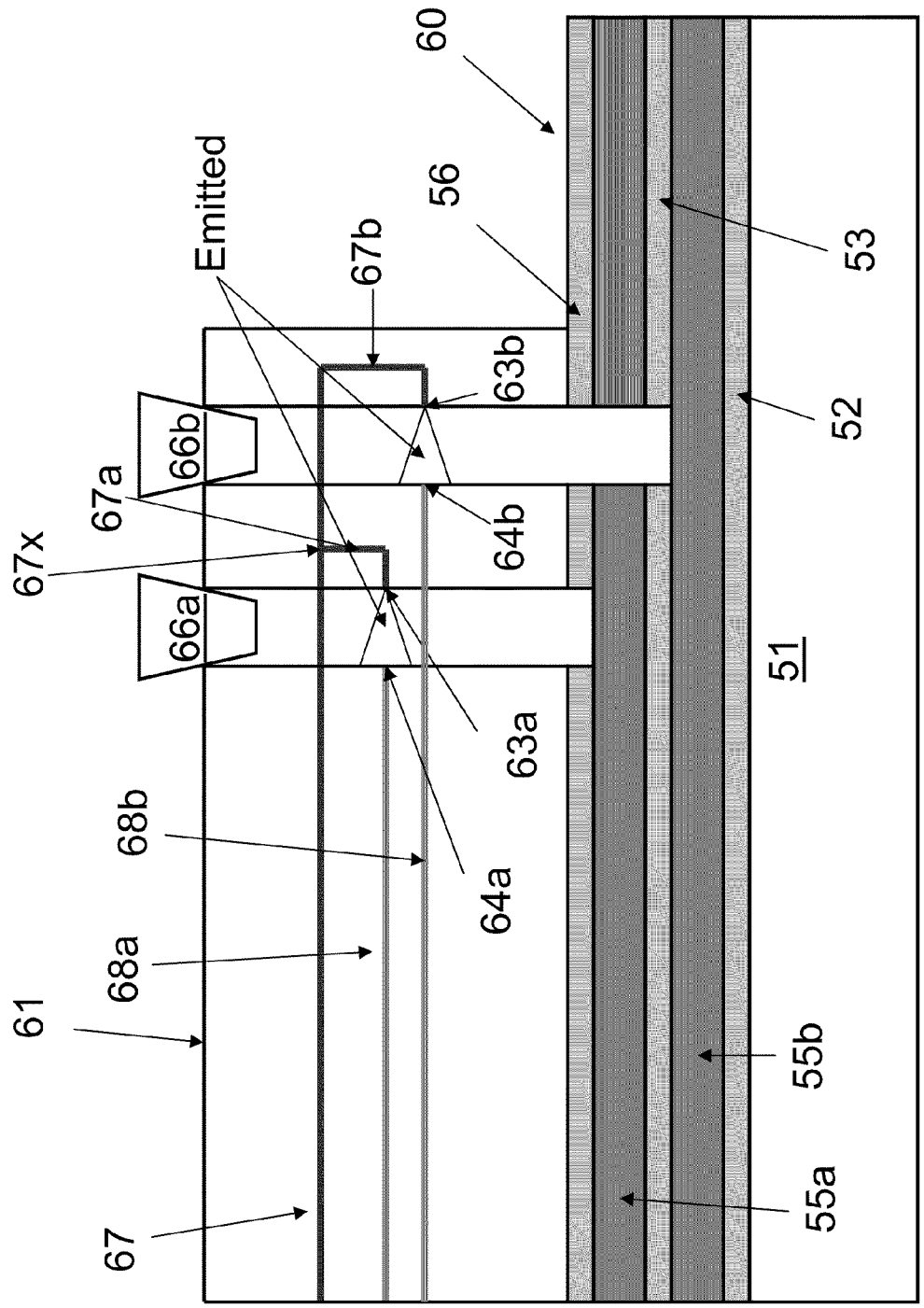

PIPE SYSTEM, A FLUID SENSING SYSTEM FOR A PIPE SYSTEM, AND A METHOD OF DETERMINING A FLUID COMPONENT IN AN ANNULUS CAVITY OF A PIPE

TECHNICAL FIELD

The present invention relates to a pipe system, a fluid sensing system for a pipe system and a method of determining a fluid component in an annulus cavity of a pipe. Basically the invention is focused on the qualitative and/or quantitative determination of one or more components in an annulus cavity of a pipe.

BACKGROUND ART

Many types of pipe systems for transporting fluids, such as aggressive fluids, are known in the art, including both onshore and offshore pipe systems, such as pipes for transporting hydrocarbon containing fluids. Often the pipe system is subjected to high and often varying pressures both within its flow channel and if used offshore also from the surrounding water in which it is used or from being trenched and covered with rocks and other covering materials.

Pipes of this type often comprise several layers for providing the pipe with a sufficient strength during use. The present invention relates in particular to a system comprising a pipe comprising a flow channel and an annular fluid cavity surrounding the flow channel. Such an annular fluid cavity is often equipped with a gas drainage valve in order to ensure that the pressure within the annular cavity does not exceed a certain selected pressure. Such a pipe with a gas drainage valve is for example described in U.S. Pat. No. 7,296,480. During use fluid components such as gasses from the medium immediately surrounding the pipe (e.g. sea water) and/or from the fluid transported in the flow channel are penetrating into the annulus. Many of these fluid components are very aggressive and in order to estimate the lifetime of the pipe it is desirable to know the qualitative and/or quantitative amount of such fluid components. Other less aggressive fluid components in the annulus can also be used in the analysis of the general state of the pipe as well as in the analysis of the fluid transported in the flow channel and the pressure/temperature conditions along the pipe. Furthermore a qualitative and/or quantitative determination of one or more fluid components in the annulus may be used to determine failure of the pipe in general such a local leakage or other fractures of one or more layers of the pipe.

The quantitative amount may be determined as the absolute quantitative amount e.g. per volume unit or it may be determined as the relative quantitative amount e.g. in relation to another fluid component, in relation to a set value, or in relation to any other value which makes sense to the skilled person.

It is therefore desirable to obtain qualitative and/or quantitative measurements of the fluid components in the annulus of the pipe, with respect to one or more selected fluid components and in particular one or more gas components.

WO 03/056313 describes a sensor system for use in the detection or measurement of at least one characteristic relating to a chemical environment in a flexible pipe. The system comprises incorporating an optical fibre along a flexible pipe—e.g. in an armouring wire; letting a gas derived from the chemical environment diffuse into the optical fibre, thereby altering the optical properties of the optical fibre; detecting and analyzing light from the optical fibre so as to determine changes in the optical properties of the optical fibre due to the in-diffusion of said gas; and deriving said at least one characteristic value representing the chemical environment from the determined changes. This system, which has never been used in practice in a flexible pipe, is however rather complicated to use as it reacts relatively slowly and it is difficult to obtain separate determination of desired fluid components. The traditional method of determining fluid components from the fluid in the annulus is still to take out samples at regular intervals and to test them in the laboratory.

The object of the invention is therefore to provide a pipe system comprising a pipe comprising a flow channel and an annular fluid cavity surrounding the flow channel and which comprises a safe and simple arrangement for obtaining qualitative and/or quantitative determinations of one or more selected fluid components in the annulus.

DISCLOSURE OF INVENTION

This object has been achieved by the invention as it is defined in the claims.

As it will be clear to the skilled reader the invention and embodiments of the invention provide several additional benefits which are explained in the following.

It should be emphasized that the term "comprises/comprising" when used in this specification is taken to specify the presence of stated features, integers, steps or components but does not preclude the presence or addition of one or more other stated features, integers, steps, components or groups thereof.

The inventors of the present invention have provided a new pipe system in which fluid in the annulus can be examined in a very simple, reliable and safe way. The pipe system comprises a pipe, a fluid sensing station and a remote light detector system. The remote light detector system ensures that there is no electricity or risk of sparks due to the detector system near the pipe. Since such pipes often are used for transportation of highly volatile and often flammable fluids such as hydrocarbons, this feature is highly beneficial for the safety of the system. The pipe comprises a flow channel and an annular fluid cavity surrounding the flow channel. The fluid sensing station comprises a sensing fluid cavity which is in fluid communication with the annular fluid cavity. In fluid communication should be taken to mean that fluid can pass directly from one part (the sensing fluid cavity) to the other part (the annular fluid cavity) which parts are then in fluid communication. In one embodiment the sensing fluid cavity is integrated and constitutes a part of the annular fluid cavity. In this embodiment the fluid in the annular fluid cavity will simultaneously be in the sensing fluid cavity, i.e. the fluid communication comprises no additional fluid pathway. In another embodiment the fluid communication between the annular fluid cavity and the sensing fluid cavity comprises a fluid pathway. This fluid pathway may optionally comprise one or more vents for controlling and/or adjusting the fluid flow in the fluid pathway.

The sensing fluid cavity comprises a light emitter and a light receiver placed at a distance from each other. The light emitter and the light receiver are optically connected to each other and optically connected to the remote light detector system.

The system according to the invention has shown to provide a very reliable detection of the most desired fluid components in a pipe annulus. The system is very simple to apply and can even be used with already installed pipe systems as it will be explained further below. The system can be used to obtain measurements at desired intervals or it may even be used for continuous determinations if desired.

The fluid to be examined may in principle be any kind of fluid, such as liquid and/or gas. In one embodiment the fluid to be examined is water, such as sea water. In one embodiment the fluid to be examined comprises a gas. In a preferred embodiment the fluid to be examined, and therefore the fluid in the sensing fluid cavity is a gas, comprising one or more gas components, such as at least one of oxygen, methane, hydrogen sulphides and carbon dioxides.

The term "a fluid component" is herein used to mean a chemical item, such as a molecule or groups of molecules e.g. oxygen, methane, hydrogen sulphides and carbon dioxides. The fluid component may be in any fluid phase, in particular in liquid form or in gas form. In most situations the fluid component will be in gas form.

In the following the invention is particularly described with the embodiment where the pipe is a flexible pipe and in particular a flexible unbonded pipe, which is also a preferred embodiment. It should, however, be clear to the skilled person that the pipe may be any pipe comprising an annulus.

The flexible pipes may in particular be for offshore use but it could also be for onshore use. The term "unbonded" means in this text that at least two of the layers of the pipe are not bonded to each other. Often unbonded flexible pipes comprise an internal sheath which forms a barrier against the outflow of the fluid which is conveyed through the pipe, and one or more armouring layers on the outer side of the internal sheath (outer armouring layer(s)). The flexible pipe may comprise additional layers such as a carcass which is an inner armouring layer to prevent the collapse of the internal sheath. An outer sheath may be provided with the object of forming a barrier against the ingress of fluids from the pipe surroundings to the armouring layers. In practice the pipe will normally comprise at least two armouring layers, which are not bonded to each other directly or indirectly via other layers along the pipe. Thereby the pipe becomes bendable and sufficiently flexible to roll up for transportation. The armouring layers are normally comprised in one or more annuli provided between internal, outer and optional intermediate sheaths.

The individual layers of the flexible pipe may e.g. be as described in "Recommended Practice for Flexible Pipe API 17B, Mar. 1, 2002" and "Specification for Unbonded Flexible Pipe 17J, Nov. 1, 1999" or any updated versions thereof.

The above-mentioned type of flexible pipes is used, among other things, for off-shore as well as some on-shore applications for the transport of fluids and gases. Flexible pipes can e.g. be used for the transportation of fluids where very high or varying water pressures exist along the longitudinal axis of the pipe, such as riser pipes which extend from the seabed up to an installation on or near the surface of the sea, pipes for transportation of liquid and gases between installations, pipes which are located at great depths on the seabed, or between installations near the surface of the sea.

An umbilical is a type of flexible pipe which is used for the transport of process liquids and hydraulic oil and for carrying light and power from an installation positioned at the surface of the sea and down to the oil wells on the seabed. Umbilicals are not directly involved in the transport of oil and gas, but may be necessary for the supply of the process liquids which, as mentioned, are to be used for the recovery of oil, as well as for the running of hydraulic pipes, electrical wires, fibre optics, etc. An umbilical may be combined with an oil/gas transporting pipe e.g. a riser to form an integrated production umbilical or an integrated service umbilical.

In one embodiment of the invention the pipe is an umbilical.

In one embodiment the pipe is a flexible pipe comprising at least two unbonded layers, preferably the pipe comprises from inside out an internal sheath, one or more armouring layers and an outer sheath, said internal sheath preferably forming a resistance or barrier against the outflow of liquid fluid which is conveyed through the pipe through said flow channel, and said outer sheath preferably forming a barrier against ingress of liquid fluids.

The pipe may comprise an internal sheath and an outer sheath, and optionally one or more intermediate sheaths. Preferably at least two of the sheaths form a barrier against fluid, and the annular fluid cavity is provided between said two barrier sheaths. The two barrier providing sheaths are in the following referred to as barrier sheaths. The two barrier sheaths may e.g. be an internal sheath and an outer sheath, an internal sheath and an intermediate sheath, an intermediate sheath and an outer sheath and/or two intermediate sheaths.

A barrier sheath should herein be understood to mean a sheath which forms a resistance or a barrier against passing of a liquid fluid and/or a gas fluid, such that a different fluid composition can be maintained on the respective sides of the barrier sheath due to the barrier properties for example for at least 24 hours under ordinary use conditions of the pipe. The barrier sheaths will typically not provide a complete barrier against gas flow, but it is often preferred that the barrier sheaths provide at least a resistance against passing of gas. The barrier sheaths preferably form at least a resistance against hydrocarbons and/or sea water and/or one or more types of gas, such as oxygen, methane, hydrogen sulphides and carbon dioxides.

The pipe may comprise one or more flexible film or foil layers such as it is generally known in the art of flexible pipes. It is preferred that at least one of said one or more flexible film or foil layers forms a resistance or barrier against fluid, the annular fluid cavity being provided between said two barrier layers selected from barrier sheaths and foil/film barrier layers.

A foil layer means a layer of a metallic or metal containing material which is sufficiently flexible such that it does not significantly increase the total stiffness of the pipe. A film layer means a layer comprising a polymeric matrix in a layer, which layer is sufficiently flexible such that it does not significantly increase the total stiffness of the pipe. A foil/film barrier layer is a foil/film layer which forms at least a resistance, such as a resistance or a barrier against passing of a liquid fluid and/or a gas fluid, such that a different fluid composition can be maintained on the respective sides of the foil/film barrier layer due to the barrier properties for at least 24 hours under ordinary use conditions of the pipe. The foil/film barrier layer preferably forms a resistance or a barrier against hydrocarbons and/or sea water and/or one or more types of gas, such as oxygen, methane, hydrogen sulphides and carbon dioxides.

The annular fluid cavity may preferably extend along the length of the pipe, such as in a length of at least 10 m, such as at least 25 m, such as at least 50 m, such as at least 100 m, such as between 50 and 3000 m. The fluid cavity will often comprise one or more armouring layers of the pipe. In this situation it is in particular desirable to obtain measurement of aggressive fluids in the annulus.

In one embodiment of the invention the annulus comprises one or more optical fibers, such as an optical fiber for monitoring temperatures along the length of the pipe and or measuring mechanical properties along the length of the pipe. Flexible pipes comprising such optical fiber for monitoring temperatures along the length of the pipe and or measuring mechanical properties along the length of the pipe are for example described in applicant's patent U.S. Pat. No. 7,024, 941 and co-pending applications DK PA 2006 01706 and DK PA 2007 01203.

The remote light detector system comprises a light source optically connected to feed the light emitter in the sensing fluid cavity. The light source is preferably optically connected to said light emitter by an optical fiber, however, it should be understood that the optical connection could comprise one or more lenses and/or one or more mirrors for directing the light beam.

In principle any light source could be applied in the present system. The light source can generally be selected in dependence on the fluid component to be detected. In one embodiment the remote light detector system comprises two or more light sources which can be used simultaneously or one by one. In order to obtain highly reliable determinations of desired fluid component(s) the light source preferably comprises at least one of a gas discharge lamp e.g. a xenon based light source, a laser, a light emitting diode (LED) and a semiconductor diode laser, preferably the light source being as laser such as a laser selected from supercontinuum lasers.

In one embodiment the light source comprises at least one of a tunable diode laser source, a quantum cascade laser (QCL), an interband cascade laser (ICL), an optical parametric oscillator (OPO). Such light sources are in particular useful for providing a modulated radiation.

In particular a broad spectral light source is preferred because by using such a broad spectral light source determination of the most important fluid components in the pipe annulus can be performed simultaneously.

In one embodiment the light source should accordingly be capable of emitting light within a broad spectrum. Thereby the remote detector system may be sensitive to a broad range of gas components, preferably including oxygen, methane, hydrogen sulphides and carbon dioxides either in gas form or when dissolved in water.

A supercontinuum laser has so far shown to be the most promising light source. In this connection a particularly preferred light source is a supercontinuum light sources, such as the supercontinuum light sources sold under the trade name Koheras SuperK™, by Koheras A/S, Denmark, which is a sister company to the applicant.

The light source may be arranged to simultaneously emit light within the whole spectral range or it may be a scanning device.

In one embodiment the light source emits light comprising wavelengths which interact with water vapour and/or one or more of the components selected from oxygen, methane, hydrogen sulphides and carbon dioxides either in gas form or when dissolved in water.

By the term "interact" is meant that the light is at least partly absorbed, is at least partly scattered and/or is at least partly subjected to another detectable change.

In one embodiment the light source emits light comprising wavelengths which interact with water vapour and/or one or more of the components selected from oxygen, methane, hydrogen sulphides and carbon dioxides either in gas form or when dissolved in water at least by absorbing at least a part of the emitted light.

In one embodiment the light source emits light comprising wavelengths which interact with water vapour and/or one or more of the components selected from oxygen, methane, hydrogen sulphides and carbon dioxides either in gas form or when dissolved in water at least by scattering at least a part of the emitted light.

In one embodiment the light source emits light comprising wavelengths in the range $10^{-19}$ to $10^{-2}$ meters, such as $10^{-7}$ to $10^{-5}$ meters e.g. 1-10 µm, or such as $10^{-9}$ to $10^{-7}$ meters, e.g. 400-600 nm. Thereby the most important fluid components may be detected.

The remote light detector comprises means for detecting the light source delivered from the light receiver. Preferably the remote light detector comprises an analyzer.

The light detector system may preferably be arranged to detect one or more fluid components using at least one of spectroscopy, spectrophotoscopy, Raman scattering, Raman spectroscopy, Resonance Raman spectroscopy, surface enhanced Raman spectroscopy, infrared spectroscopy and ultra-violet spectroscopy.

The detector may preferably perform the detection using at least one of the following types of light-matter interaction: Elastic scattering such as Rayleigh scattering, Mie scattering, quasielastic light scattering such as Doppler shifted light or Brillouin scattering, inelastic scattering such as Raman scattering, surface enhanced Raman scattering, absorption of ultra-violet, visible or infrared light.

In one embodiment the remote light detector comprises an analyzer. The analyzer may in principle be of any type capable of analyzing at least a fraction of light delivered from the light receiver. The analyzer may for example be capable of performing at least one of a spectral analysis, a temporal analysis and a power level analysis. In this connection a spectral analysis means an analysis of one or more changes (relative along the width of the wavelength specter or in absolute power values) of the wavelength specter of the light delivered from the light receiver compared to the emitted light; a temporal analysis means an analysis of one or more variations of the specter over time; and a power level analysis means an analysis of the absolute light intensity (power) of one or more wavelengths.

The analyzer should preferably be optically connected to said light receiver in said sensing fluid cavity by an optical fiber and optionally one or more mirrors and/or lenses may be included in the optical path providing the optical connection.

In one embodiment the analyzer is capable of analyzing at least a fraction of light delivered from said light receiver. As an example of a useful analyzer a spectrometer can be mentioned, such as a spectrophotometer or a radiometer.

The analyzer may be an analyzer selected in particular to be used in connection with pipes transporting hydrocarbons, such as crude oils and gasses. In one embodiment the analyzer is selected such that it is capable of analyzing light comprising wavelengths which interact with or result from an interaction with water vapour and/or one or more of the components selected from oxygen, methane, hydrogen sulphides and carbon dioxides either in gas form or when dissolved in water.

In one embodiment the analyzer is selected such that it is capable of analyzing light comprising wavelength which are at least partly absorbable by water vapour and/or one or more of the components selected from oxygen, methane, hydrogen sulphides and carbon dioxides either in gas form or when dissolved in water.

In one embodiment the analyzer is selected such that it is capable of analyzing light comprising wavelengths which are at least partly scatterable by water vapour and/or one or more of the components selected from oxygen, methane, hydrogen sulphides and carbon dioxides either in gas form or when dissolved in water.

In one embodiment the analyzer is selected such that it is capable of analyzing light comprising wavelengths in the range $10^{-10}$ to $10^{-2}$ meters, such as $10^{-7}$ to $10^{-5}$ meters e.g. 1-10 µm, or such as $10^{-9}$ to $10^{-7}$ meters, e.g. 400-600 nm.

Based on the above teaching the skilled person will be capable of selecting a useful analyzer. As specific examples of analyzers can be mentioned the spectrometers marketed by StellarNet Inc. Florida, USA.

In one embodiment the remote light detector system comprises a light source and an analyzer which are coupled to each other e.g. optically or digitally. Thereby the fluid sensing station may be arranged to be capable of comparing the wavelengths and/or intensities of the emitted light with the corresponding wavelengths and/or intensities of the received light. By comparing the spectrum profile, intensities of local wavelengths and/or intensities along the spectrum the analyzer may be used to perform quantitative and/or qualitative determinations of one or more fluid components in the annulus cavity.

In one embodiment the sensing fluid cavity comprises a light emitter and a light receiver placed at a distance from each other, and a gas sensor is placed between the light emitter and the light detector, so that the light emitter and the light receiver are optically connected to each other via said gas sensor. The gas sensor may preferably be arranged such in relation to the light emitted from the light emitter that a light beam emitted from said light emitter into said gas sensor will be modified in said gas sensor in dependence on the contents of the gas in said sensing fluid cavity.

In principle the gas sensor may in one embodiment constitute and/or comprise the sensing fluid cavity.

In one embodiment the gas sensor is a photoacoustic spectroscope (PAS) such as a Quartz-enhanced photoacoustic spectroscope (QEPAS)

Photoacoustic spectroscopy (PAS) is an established method of experimental physics. It is based on detection of sound waves produced in an absorbing medium when the medium is illuminated by modulated radiation. A common approach used to detect the acoustic signal generated by modulated laser radiation in a weakly absorbing gas utilizes an acoustic resonator filled with the gas sample. Accordingly the sensing fluid cavity should at least comprise the acoustic resonator of the gas sensor in the form of a PAS.

In one embodiment the PAS requires an electrical power supply. This energy for this electrical power supply may preferably be provided by the light emitter or it may be provided by a separate source e.g. a separate light source.

In one embodiment the power supply to the gas sensor (e.g. PAS, such as QEPAS described below) is provided via an electrical wire. The electrical wire may be explosion protected/fault current protected e.g. by providing it with an electrical short so that it doesn't ignite a hazardous atmosphere causing an explosion. Further more the wire may be physically protected e.g. by packing it totally or partly in one or more layers of steel, aluminium and/or fiberglass. In one embodiment the power supply has an effect of from about 0.1 to about 1 Watt. The power may e.g. be provided as a DC low current such as from about 1-50 V—e.g. from about 2 to about 10 V and a current of from about 10 to about 1000 mA, e.g. from about 50 to about 200 mA. The electrical power may be constantly turned on or it may be regulated to be turned on only with intervals in which measurements are performed.

A PAS sensor provides is a highly sensitive sensor for gas and trace gas analysis. The photoacoustic signal is directly proportional to the optical power absorbed by the sample. The proportionality factor depends on the sensitivity of the active sensing element which may for example be a microphone.

In a preferred embodiment the PAS is a Quartz-enhanced PAS (QEPAS) in which a quartz crystal e.g. in the form of a fork, serves as a resonant microphone.

The QEPAS may for example comprise one or more clock tuning forks (TF) which act as the resonant microphone(s).

A QEPAS gas sensor is very stable and has a very low noise sensitivity which is highly desirable in the present pipe system.

In one embodiment the where the system comprises a PAS and a light source optically connected to feed the light emitter in the sensing fluid cavity, the light source is a laser source capable of being modulated.

In one embodiment the where the system comprises a PAS and a light source optically connected to feed the light emitter in the sensing fluid cavity, the light source is a tunable laser source.

Examples of useful light sources for feeding a PAS are a tunable diode laser source, a quantum cascade laser (QCL), an interband cascade laser (ICL) and an optical parametric oscillator (OPO).

In one embodiment wherein the sensing fluid cavity comprises a gas sensor in the form of a PAS, the remote light detector system is detecting one or more fluid components by analyzing the signal received from the light receiver. The remote light detector system may for example comprise an analyser capable of detecting the energy absorbed in the gas at one or more wavelength, e.g. by determining the energy absorbed in the gas as a function of wavelength over a selected range of wavelengths.

Further information about PAS and in particular QEPAS can be obtained from the articles:

A. K. Y. Ngai et al. "*Continuous wave optical parametric oscillator for quartz-enhanced photoacoustic trace gas sensing*". Appl. Phys. B 89, 123-128 (2007).

A. A. Kosterev et al. " *Ultrasensitive gas detection by quartz-enhanced photoacoustic spectroscopy in the fundamental molecular absorption bands region*". Appl. Phys. B 80, 133-138 (2005).

Rafal Lewicki et al. "*QEPAS based detection of broadband absorbing molecules using a widely tunable, cw quantum cascade laser at 8.4 μm.*" 2007 *Optical Society of America.* 11 June 2007/Vol. 15, No. 12/*OPTICS EXPRESS* 7357-7366.

In one embodiment the gas sensor is an OPO-QEPAS as described in section 2 of A. K. Y. Ngai et al. "Continuous wave optical parametric oscillator for quartz-enhanced photoacoustic trace gas sensing". Appl. Phys. B 89, 123-128 (2007).

In order to ensure a low risk of ignition of flammable fluids escaping from the pipe, the distance between at least one and preferably all active elements of the remote light detector system and the fluid sensing station should preferably be at least 2 m, such as at least 5 m, such as at least 10 m, such as at least 25 m: The active elements are herein meant to mean elements using electricity and/or light generating elements, light sources and analyzers.

The distance between the active element of the remote light detector system and the fluid sensing station is measured as the shortest distance the light signal must travel from the active element to the sensing fluid cavity of the fluid sensing station. This may for example be equal to the length of a fiber transporting light from the light source to the light emitter or equal to the length of a fiber transporting light from the light receiver to the analyzer.

In one embodiment the remote light detector system is placed at a distance from the fluid sensing station which in optical connection is at least 5 m, such as at least 10 m, such as at least 25 m. In this situation the distance between the remote light detector system and the fluid sensing station is measured as the shortest distance a light signal must travel from the remote light detector system to the sensing fluid cavity of the fluid sensing station.

In one embodiment the remote light detector system is placed at a distance from the pipe which is at least 2 m, such as at least 5 m, such as at least 10 m, such as at least 25 m. In this situation the distance between the remote light detector system and the pipe is measured as the shortest distance between said two elements.

It is generally preferred that the remote light detector system is collected in a single unit, e.g. a single unit placed in a laboratory on board a ship or on an oil platform. However, in certain situations it may be desired to have the light detector system separated into two or more units, for example in situations where the light source is very sensitive and needs special protection e.g. against vibrations.

In one embodiment the remote light detector system comprises two or more units placed side by side or at a distance from each other. In this situation it will be simpler to replace and/or change one unit without replacing and/or changing other units of the remote light detector system.

In a preferred embodiment the remote light detector system comprises at least one light source and at least one analyzer and the remote light detector system is optically connected to two or more fluid sensing stations. This embodiment provides a very cost effective solution in situations where fluids from two or more annular cavities and/or from different sections of the same annular cavity are to be analyzed quantitatively and/or qualitatively with respect to one or more fluid components. In this embodiment the analyzer should preferably be optically coupled to two or more light receivers and/or the light source should preferably be optically coupled to two or more light emitters.

It is well known in the art to couple light from one light source into two or more emitting units. This may for example be performed using a splitter or alternatively the light source may switch between feeding the two or more units.

Also it is well known in the art to couple light from two or more units, here from two or more light receivers, into one optical path, e.g. in the form of a fiber or another waveguide, e.g. using a coupler. Alternatively the two or more light receivers may independently of each other transfer the received light to the analyzer for analysis.

As it will be clear to the skilled person the remote light detector system may comprise any number of light sources and analyzers.

In one embodiment the remote light detector system comprises at least two light sources and one, two or more analyzers. The remote light detector system is preferably optically connected to two or more fluid sensing stations, and preferably the analyzer is optically coupled to two or more light receivers and/or said light source is optically coupled to two or more light emitters.

In most situations it will be sufficient to have one single analyzer. Such analyzers are generally fast and reliable, and may analyze light within a very broad wavelength spectrum. However, dependent on the light source selected it may de desirable to have two or more light sources to thereby be capable of covering a wavelength spectrum which makes it possible to quantitatively and/or qualitatively determine one or more fluid components.

Also it will be clear to the skilled person that the pipe system may comprise any number of light detector systems. Accordingly, in one embodiment the pipe system comprises two or more remote light detector systems, said two or more remote light detector systems may or may not be interconnected, such as optically interconnected.

In one embodiment the pipe system comprises two or more fluid sensing stations with respectively one or more sensing fluid cavities. The sensing fluid cavities of said two or more fluid sensing stations are in fluid communication with one or more annular fluid cavities. The two or more fluid sensing stations are in one embodiment arranged such that their respective fluid sensing station(s) are in fluid communication with the same annular fluid cavities but placed with a distance from each other—e.g. 50 meters distance or more. In one embodiment the two or more fluid sensing stations are arranged such that their respective fluid sensing station(s) are in fluid communication with different annular fluid cavities of the same pipe.

In one embodiment the pipe system comprises two or more annular fluid cavities. The two or more annular fluid cavities may preferably be in fluid communication with one or more sensing fluid cavities. In this embodiment the pipe system may for example comprise two or more fluid sensing stations which are arranged such that their respective fluid sensing station(s) are in fluid communication with the respective annular fluid cavities of the same pipe.

In one embodiment the pipe system comprises two or more annular fluid cavities, and the two or more annular fluid cavities are in fluid communication with one single sensing fluid cavity. In this embodiment the fluid from the two or more annular fluid cavities may be mixed in the sensing fluid cavity, i.e. the determination of one or more fluid components is performed on a mixture of fluids from the two or more annular fluid cavities. Alternatively the fluid communication between the two or more annular fluid cavities and the sensing fluid cavity is adjusted such that the fluid from the two or more annular fluid cavities is allowed to flow into the sensing fluid cavity in a sequential manner i.e. first the fluid from one annular fluid cavity, followed by fluid from a second annular fluid cavity and so forth.

Often the annular fluid cavity will be equipped with a pressure adjusted valve gas exit for avoiding the pressure within the annulus to increase over a certain selected pressure. Such pressure adjusted valve may for example be arranged in an end fitting coupled to one of the ends of the pipe.

In one embodiment one or more valves, e.g. pressure adjusted valve(s) are arranged in the sensing fluid cavity to control/adjust the pressure in said sensing fluid cavity.

In one embodiment one or more filters, e.g. filters preventing passing of liquids and/or selected gas components are arranged in the sensing fluid cavity to prevent selected components from exiting the sensing fluid cavity and/or to reduce the amount of selected components exiting the sensing fluid cavity.

As indicated above the fluid sensing station is in one embodiment integrated in the pipe, e.g. as described above. The sensing fluid cavity may be provided by a section of the annular fluid cavity.

In one embodiment the pipe comprises an end fitting, and the sensing fluid cavity is provided in said end fitting.

An end fitting is a fitting provided at the end of the pipe or a fitting connecting two length sections of the pipe to each other.

Such end fittings are generally known in the art. Examples of end fittings can be found in WO04085905, U.S. Pat. No. 6,412,825 and U.S. Pat. No. 6,923,477.

Usually the pipe will comprise an end fitting in each of its ends. The end fitting may e.g. be an ordinary end fitting which is usually adapted to connect the pipe to another unit e.g. to a ship or a plat form for ejecting the fluid passing through the flow channel of the pipe into a tank or similar. In one embodiment the end fitting is a double end-fitting arranged to be coupled to two pipes for connecting the pipes.

In one embodiment where the pipe comprises an end fitting, and the sensing fluid cavity is provided in said end fitting (i.e. integrated into said end fitting), the sensing fluid cavity is in fluid communication with the annular fluid cavity of the pipe connected to the end-fitting. In one embodiment a valve and/or a filter is arranged between the sensing fluid cavity and the annular fluid cavity. In one embodiment a valve and/or a filter is arranged between the sensing fluid cavity and an excess opening in the fluid cavity through which fluids, preferably gas can escape. By these various valves and/or filters pressure and/or fluid composition can be adjusted in the sensing fluid cavity In one embodiment the fluid sensing station is external to the pipe, in the following called an external fluid sensing station. This embodiment permits the pipe system of the present invention to be used in a very flexible manner. Furthermore the external fluid sensing station may be connected to existing pipes, and even pipes in the form of for example risers which have already been deployed. The fluid sensing station may in this embodiment be incorporated in a box which may e.g. be adapted to mount directly to the pipe e.g. to an end fitting of a pipe.

In one embodiment where the pipe comprises an external fluid sensing station the pipe further comprises an access opening into its annular fluid cavity through which the external sensing fluid cavity is in fluid communication with this annular fluid cavity. The said access opening may preferably be provided with a valve and/or a filter e.g. as described above.

In one embodiment where the pipe comprises an external fluid sensing station the pipe further comprises an end fitting, and the access opening into the annular fluid cavity is provided via this end fitting.

In one embodiment where the pipe comprises an external fluid sensing station this external fluid sensing station is fixed to or is adapted to be fixed to said end fitting preferably by use of one or more of a snap-lock and a bolt-nut arrangement. This embodiment is particularly simple to mount, which additionally makes is simple to replace the external fluid sensing station in case one or more units in the external fluid sensing station should be damaged or in other way cease to work properly.

In one embodiment where the pipe comprises an external fluid sensing station this external fluid sensing station is connected to said end fitting, via a tube fixed to respectively said fluid sensing station and said end fitting. This embodiment may be very beneficial in situations where access to the pipe and the end fitting of the pipe is difficult or limited. The tube may e.g. be connected to one or both of the external fluid sensing stations and the end fitting by for example a snap-lock and/or a bolt-nut arrangement.

In order to provide an optimal detection it is desired that the sensing fluid cavity comprises the light emitter optically connected to the light receiver. The optical connection may be direct (the optical connection between the light emitter and the light receiver is provided by a light path with no intermediate materials beyond the fluid in the sensing fluid cavity) or via one or more mirrors and/or one or more lenses (the optical connection between the light emitter and the light receiver is provided by a light path with one or more interposed mirrors and/or one or more interposed lenses).

In one embodiment the optical connection between the light emitter and the light receiver is provided by a light path comprising one or more interposed mirrors. Thereby the exposure length (see below) may be increased without increasing the size of the sensing fluid cavity, i.e. a long exposure length can be obtained in a relatively small sensing fluid cavity. The mirrors may also be used to adjust the length of the exposure length.

In one embodiment the optical connection between the light emitter and the light receiver is provided by a light path comprising one or more interposed lenses. The one or more lenses may be arranged to spread the light or more preferably to collect the light to be transmitted to the light receiver, thereby increasing the sensitivity of the detection of the system.

The optical connection between the light emitter and the light receiver is provided by a light path having a length which will normally be identical with the exposure length, which is the length where the light providing the optical connection is exposed to a fluid in said sensing fluid cavity. The exposure length should be sufficiently long for a determination to be performed. For example the exposure lengths may preferably be at least 1 mm, such as at least 5 mm, such as between 1 and 500 cm.

The exposure length may be fixed—which provides a simple solution or it may be adjustable which may broaden the number of different fluid components which can be determined quantitatively and/or qualitatively by said pipe system.

As mentioned above it is desired that the pipe is a flexible pipe. The pipe may be an onshore pipe e.g. for transporting aggressive chemicals e.g. crude oil, cracked oil, gasses and similar.

The pipe system of the invention is in particular beneficial if the pipe is an offshore pipe, for example an offshore pipe applied to transfer a fluid from one offshore station, such as from sea bed, to an onshore station or another offshore station, such as a platform or a ship. Offshore lines are often divided into two categories, namely flow lines for transporting fluids along the seabed, e.g. as trenched pipes or pipes placed onto the sea bed, and risers for use in transporting fluids vertically in the sea often from a seabed installation to a sea surface installation.

The pipe may be a flow line. However, preferably the pipe is a riser pipe.

In one embodiment where the pipe is a riser, the riser comprises an end fitting for connecting to an offshore station, such as a platform or a ship, the fluid sensing station is integrated in the end-fitting or being in fluid communication with the annular fluid cavity via this end-fitting, e.g. as described above, and the remote light detector system is placed at said offshore station.

In one embodiment where the pipe is a riser, the riser comprises an end fitting, connecting two length sections of the pipe to each other. The pipe is further connected to an offshore station, such as a platform or a ship. The said fluid sensing station is integrated in the connecting fitting or is in fluid communication with the annular fluid cavity via this end fitting, e.g. as described above, and the remote light detector system is placed at said offshore station.

The invention also relates to a fluid sensing system for sensing a fluid in an annulus cavity of a pipe. The fluid sensing system comprises a fluid sensing station and a remote light detector system. The fluid sensing station comprises a sensing fluid cavity comprising a light emitter and a light receiver placed at a distance from each other and optically connected to each other.

The remote light detector system comprises a light source and an analyzer. The light emitter is optically connected to the light source. The light receiver is optically connected to the analyzer. The fluid sensing station is arranged to be connected to a pipe with an annular fluid cavity to provide a fluid communication between the annular fluid cavity and the sensing fluid cavity.

The various elements and their relations/interconnections with each other of the fluid sensing system may be as described above for the pipe system, except that the sensing fluid cavity is not integrated in the pipe. For example the light source may be as described above, the light detector may be as described above, the analyzer may be as described above, the pipe structure may be as described above and the sensing fluid cavity may be as described above except that it is not integrated in the pipe. Also, in one embodiment the fluid sensing system may comprise a gas sensor as described for the pipe system above.

The fluid sensing system may preferably be adapted to be connected to a pipe comprising an access opening into an annular fluid cavity such as described above. The sensing fluid cavity is adapted to be in fluid communication with the annular fluid cavity through this access opening.

The invention also relates to a method of determining a fluid component in an annular fluid cavity of a pipe comprising the use of a pipe system as described above.

The determination may in one embodiment be a qualitative determination of the presence of one or more components, preferably selected from the group of oxygen, methane, hydrogen sulphides and carbon dioxides either in gas form or when dissolved in water. These components are alone or in combinations the most aggressive ones in the transport of crude oils, and accordingly it is desired that the method includes determining at least qualitatively the presence of the major part, preferably all of said fluid components.

The determination may in one embodiment be a quantitative determination of the amount of one or more components, preferably selected from the group of oxygen, methane, hydrogen sulphides and carbon dioxides either in gas form or when dissolved in water. It is in this embodiment desired that the method includes quantitative determination of the major part, preferably all of said fluid components.

The determination may be performed continuously or at predetermined intervals.

In one embodiment the system is connected to an alarm which is activated if the results deviate from a set point or deviate significantly from previous determinations.

In one embodiment the determination is performed using different light exposure distances between light emitter and light receiver.

BRIEF DESCRIPTION OF DRAWINGS

The invention will be explained more fully below in connection with a preferred embodiment and with reference to the drawings in which:

FIG. 4 is a schematic side view of a first pipe system of the invention.

FIG. 4a is a schematic side view of a variation of the first pipe system shown in FIG. 4

FIG. 6a is a schematic side view of a variation of the third pipe system shown in FIG. 6.

FIG. 7 is a schematic side view of a fourth pipe system of the invention.

Figure 1:
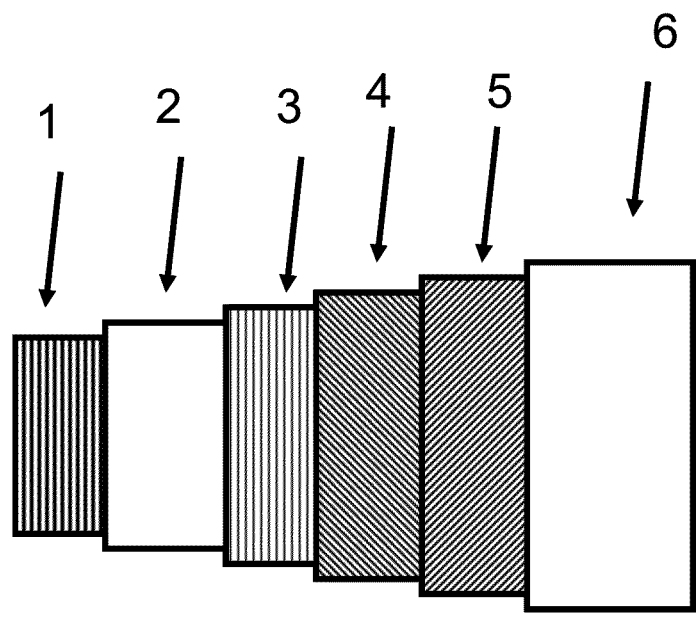
FIG. 1 is a schematic side view of a pipe with a carcass.

Further scope of applicability of the present invention will become apparent from the detailed description given hereinafter. However, it should be understood that the detailed description and specific examples, while indicating preferred embodiments of the invention, are given by way of illustration only, since various changes and modifications within the spirit and scope of the invention will become apparent to those skilled in the art from this detailed description.

The figures are schematic and simplified for clarity, and they just show details which are essential to the understanding of the invention, while other details are left out. Throughout, the same reference numerals are used for identical or corresponding parts.

The flexible pipe shown in FIG. 1 comprises an internal sheath 2, often also called an inner liner, e.g. of cross linked PE. Inside the inner liner 2 the pipe comprises an inner armouring layer 1, called a carcass. On the outer side of the inner liner 2, the flexible pipe comprises three outer armouring layers 3, 4, 5. The inner armouring layer 3 closest to the inner liner 2, is a pressure armouring layer 3, made from profiles and/or strips wound at a steep angle to the centre axis of the pipe, e.g. close to 90 degrees. Around the pressure armouring layer 3, the pipe comprises a pair of cross wound tensile armouring layers 4, 5, made from wound profiles and/or strips. These tensile armouring layers 4, 5 are normally cross wound with equal or different angles of 70 degrees or less, typically 60 degrees or less, such as 55 degrees or less, such as between 20 and 55 degrees. The pipe further comprises an outer polymer layer (outer sheath) 6 protecting the armouring layer mechanically and/or against ingress of sea water.

Between the internal sheath 2 and the outer sheath is provided an annulus, also called an annulus cavity. In this annulus cavity the pressure armouring layer 3 and the tensile armouring layers 4, 5 are placed. The armouring layers are not fluid tight.

Figure 2:
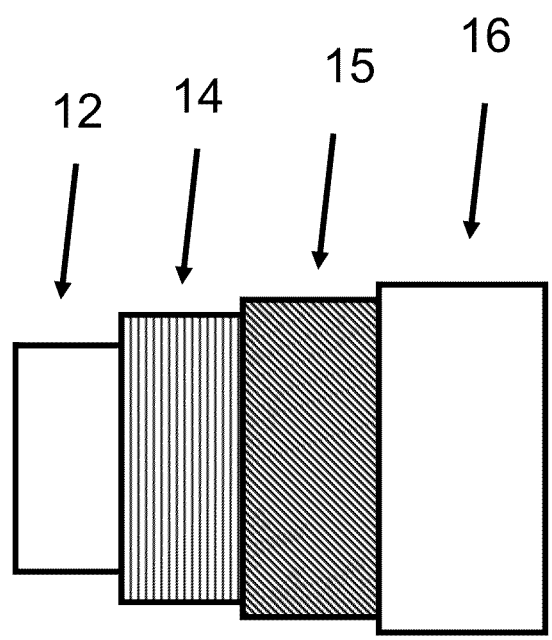
FIG. 2 is a schematic side view of a pipe without a carcass.

FIG. 2 shows another pipe design. This flexible pipe comprises an inner liner 12 and a pair of outer armouring layers, 14, 15, in the form of profiles and/or strips wound around the inner liner 12. The two armouring layers are cross wound at an angle to the centre axis of the pipe of close to 55 degrees, typically one of the layers is wound at an angle slightly less than 55 degrees, e.g. between 52 and 55 degrees, and the other one of them is wound at an angle slightly more than 55 degrees e.g. between 55 and 57. The pipe further comprises an outer polymer layer 16 protecting the armouring layer mechanically and/or against ingress of sea water.

Between the internal sheath 12 and the outer sheath is provided an annulus, also called an annulus cavity. In this annulus cavity the outer armouring layers 14, 15 are placed. The armouring layers are not fluid tight.

Figure 3:
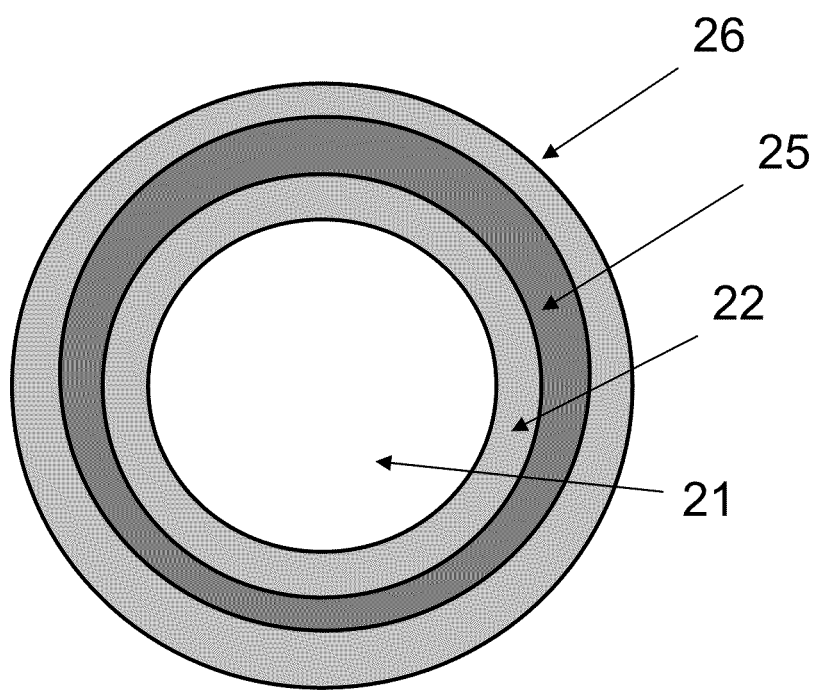
FIG. 3 is a cross-sectional view of a pipe.

FIG. 3 shows in a schematic view a cross-sectional cut of a pipe. The pipe comprises an inner sheath 22, forming a flow channel 21, and an outer sheath 26. The inner sheath 22 and the outer sheath are barrier sheaths as defined above, and provide an annular cavity 25 between them. The annular cavity may comprise not shown armouring layers.

The pipe of the pipe system of the invention may for example be as shown in any one of FIGS. 1-3.

FIG. 4 is a schematic side view of a first pipe system of the invention. The pipe system comprises a pipe 30 for example as shown in FIG. 3. The pipe comprises an end fitting 31, with an integrated sensing fluid cavity 32 providing the fluid sensing station. The sensing fluid cavity 32 comprises a light emitter 33 and a light receiver 34 placed at a distance from each other, so that when light is emitted from the light emitter 33, at least a part of the light will be received by the light receiver 34 after having interacted with the fluid in the sensing fluid cavity 32. The sensing fluid cavity 32 is in fluid communication with the annulus 25 via an opening 35 in the pipe into the annulus 25. The sensing fluid cavity comprises a valve 36 for adjusting and/or controlling the pressure in the sensing fluid cavity 32. Simultaneously the valve 36 may ensure that the pressure within the annulus cavity 25, does not increase above a desired level.

The pipe system further comprises a not shown remote light detector system. The remote light detector system comprises a light source as described above feeding light to the light emitter 33 via an optical fiber 37. The remote light detector system further comprises a detector as described above receiving light collected by the light receiver 34 via an optical fiber 38.

FIG. 4a is a schematic side view of a variation of the first pipe system shown in FIG. 4. The reference numbers in FIG. 4a have the same meaning as in FIG. 4.

The pipe system in FIG. 4a further comprises a gas sensor in the form of a photoacoustic spectroscope (PAS) preferably a Quartz-enhanced photoacoustic spectroscope (QEPAS) arranged in the sensing fluid cavity so that the light emitter 34 and the light receiver 33 are optically connected to each other via the PAS gas sensor. In the shown embodiment the PAS gas sensor is placed inside the sensing fluid cavity. In another not shown embodiment the PAS gas sensor constitutes or comprises the sensing fluid cavity, so that at least an acoustic resonator of the PAS gas sensor is in contact with the gas to be detected.

The pipe system in FIG. 4a may further comprise a not shown temperature detector and/or regulator for to avoid or reduce any undesired or unknown noise or fault due to temperature influences.

The pipe system in FIG. 4a may additionally comprise a not shown pressure detector for optimizing the analysis of the signal obtained from the gas sensor.

Figure 5:
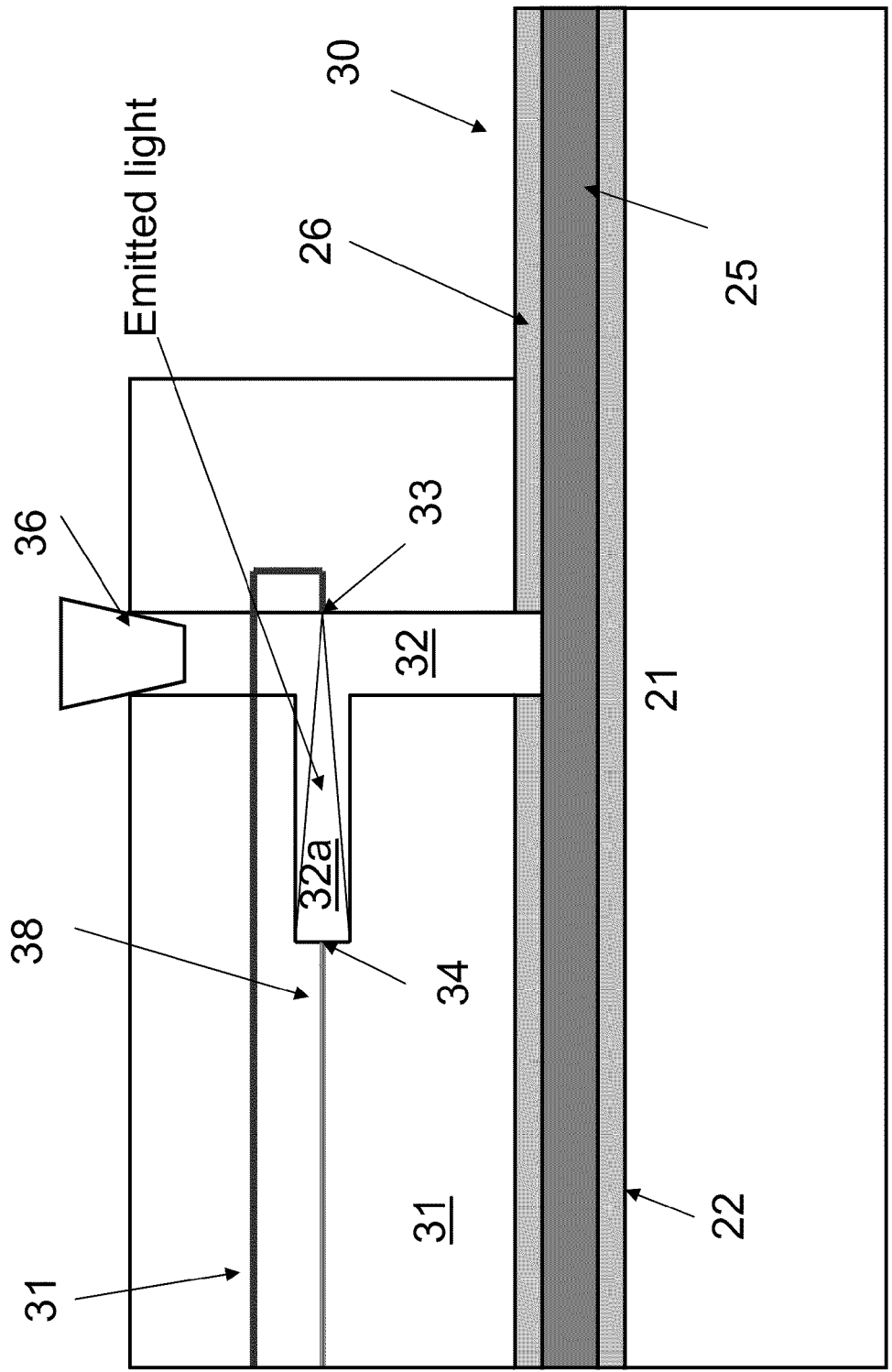
FIG. 5 is a schematic side view of a second pipe system of the invention.

FIG. 5 is a schematic side view of a second pipe system of the invention. The pipe system in FIG. 5 is similar to the pipe system shown in FIG. 4 except that the sensing fluid cavity 32 comprises an additional section 32a in which the light receiver 34 is placed. Thereby the exposure length, which here is equal to the distance between the light receiver 33 and the light receiver 34, can be increased.

Figure 6:
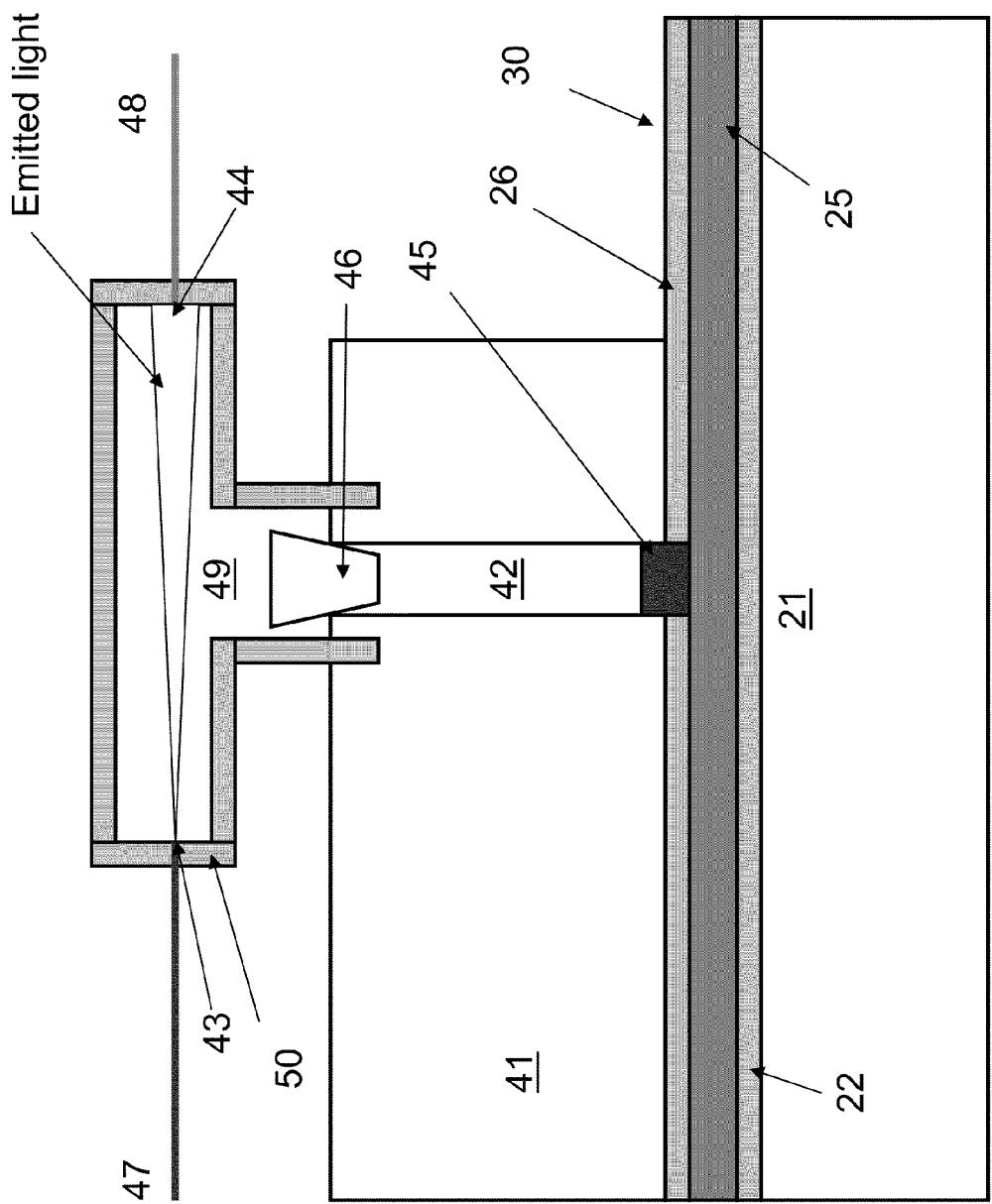
FIG. 6 is a schematic side view of a third pipe system of the invention.

FIG. 6 is a schematic side view of a third pipe system of the invention. The pipe system of FIG. 6 comprises a pipe 30 similar to the pipe in the pipe system shown in FIG. 4. The pipe comprises an end fitting 41, with an access channel 42 providing an access path to the annulus cavity 25. The pipe 30 comprises an access opening to the access channel 42 and a filter 45 is arranged in the access opening to prevent liquid and particles from escaping from the annular cavity 25. The pipe system further comprises a fluid sensing station 50 placed externally to the pipe 30 and connected to the end-fitting e.g. by use of a not shown bolt-nut arrangement.

The fluid sensing station 50 comprises a sensing fluid cavity 49 which is arranged to be in fluid communication with the annular cavity 25 via the access channel 42 in the end fitting. In the passage between the end fitting access channel 42 and the sensing fluid cavity 49 a valve 46 is arranged in order to adjust and/or control the pressure in the annular cavity 25 and optionally in the sensing fluid cavity 49. The fluid sensing station 50 further comprises a not shown valve to further adjust and/or control the pressure in the sensing fluid cavity 49. The sensing fluid cavity 49 comprises a light emitter 43 and a light receiver 44 placed at a distance from each other, so that when light is emitted from the light emitter 43, at least a part of the light will be received by the light receiver 44 after having interacted with the fluid in the sensing fluid cavity 49.

The pipe system in FIG. 6 further comprises a not shown remote light detector system. The remote light detector system comprises a light source as described above for feeding light to the light emitter 43 via an optical fiber 47. The remote light detector system further comprises a detector as described above for receiving light collected by the light receiver 44 via an optical fiber 48.

FIG. 6 is a schematic side view of a variation of the pipe system shown in FIG. 6. The reference numbers in FIG. 6a have the same meaning as in FIG. 6.

The fluid sensing station 50a in FIG. 6a differs slightly from the fluid sensing station 50 in FIG. 6 in that it further comprises a gas sensor in the form of a photoacoustic spectroscope (PAS), preferably a Quartz-enhanced photoacoustic spectroscope (QEPAS) arranged in the sensing fluid cavity 49a so that the light emitter 43a and the light receiver 44a being optically connected to each other via the PAS gas sensor. The fluid sensing station 50a further comprises a not shown valve to further adjust and/or control the pressure in the sensing fluid cavity 49a. If the PAS gas sensor requires electricity this electricity may preferably be generated from a part of the energy supplied by the light emitter 43a. The generator may preferably be an integrated part of the PAS gas sensor.

In the shown embodiment the PAS gas sensor is placed inside the sensing fluid cavity 50a, which as indicated can be very small. In another not shown embodiment the PAS gas sensor constitutes or comprises the sensing fluid cavity, so that at least an acoustic resonator of the PAS gas sensor is in contact with the gas to be detected.

The pipe system in FIG. 6a may further comprise a not shown temperature detector and/or regulator for to avoid or reduce any undesired or unknown noise or fault due to temperature influences.

The pipe system in FIG. 6a further comprises a not shown remote light detector system which is arranged to analyse the result obtained from the light receiver 44a via the optical fiber 48.

FIG. 7 is a schematic side view of a fourth pipe system of the invention. The pipe system comprises a pipe 60 comprising two separate annulus cavities 55a, 55b provided by three barrier layers in the form of an inner sheath 52, forming a flow channel 51, an intermediate sheath 53, and an outer sheath 56. The annular cavities may comprise not shown armouring layers e.g. as explained above.

The pipe comprises an end fitting 61, with an integrated fluid sensing station in the form of two integrated sensing fluid cavities 62a, 62b. Each of the sensing fluid cavities 62a, 62b comprises a light emitter 64a, 64b and a light receiver 64a, 64b placed at a distance from each other, so that when light is emitted from the light emitter 64a, 64b, at least a part of the light will be received by the light receiver 64a, 64b after having interacted with the fluid in the respective sensing fluid cavities 62a, 62b. The two sensing fluid cavities 62a, 62b respectively are in fluid communication with the annulus cavities 55a, 55b via respective openings 54a, 54b in the pipe into the respective annulus cavities 55a, 55b. Each of the sensing fluid cavities 62a, 62b comprises a valve 66a, 66b for adjusting and/or controlling the pressure in the respective sensing fluid cavities 62a, 62b. Simultaneously the valves 66a, 66b may ensure that the pressure within the respective annulus cavities 55a, 55b, does not increase above a desired level.

The pipe system in FIG. 7 further comprises a not shown remote light detector system. The remote light detector system comprises a light source as described above for feeding light to the light emitters 63a, 63b via an optical fiber 67 which comprises a splitter 67x, splitting the transmitted light into the optical fibers optically connected to the respective light emitters 63a, 63b. The remote light detector system further comprises one or two detectors as described above for receiving light collected by the respective light receivers 64a, 64b via respective optical fibers 68a, 68b.

Figure 8:
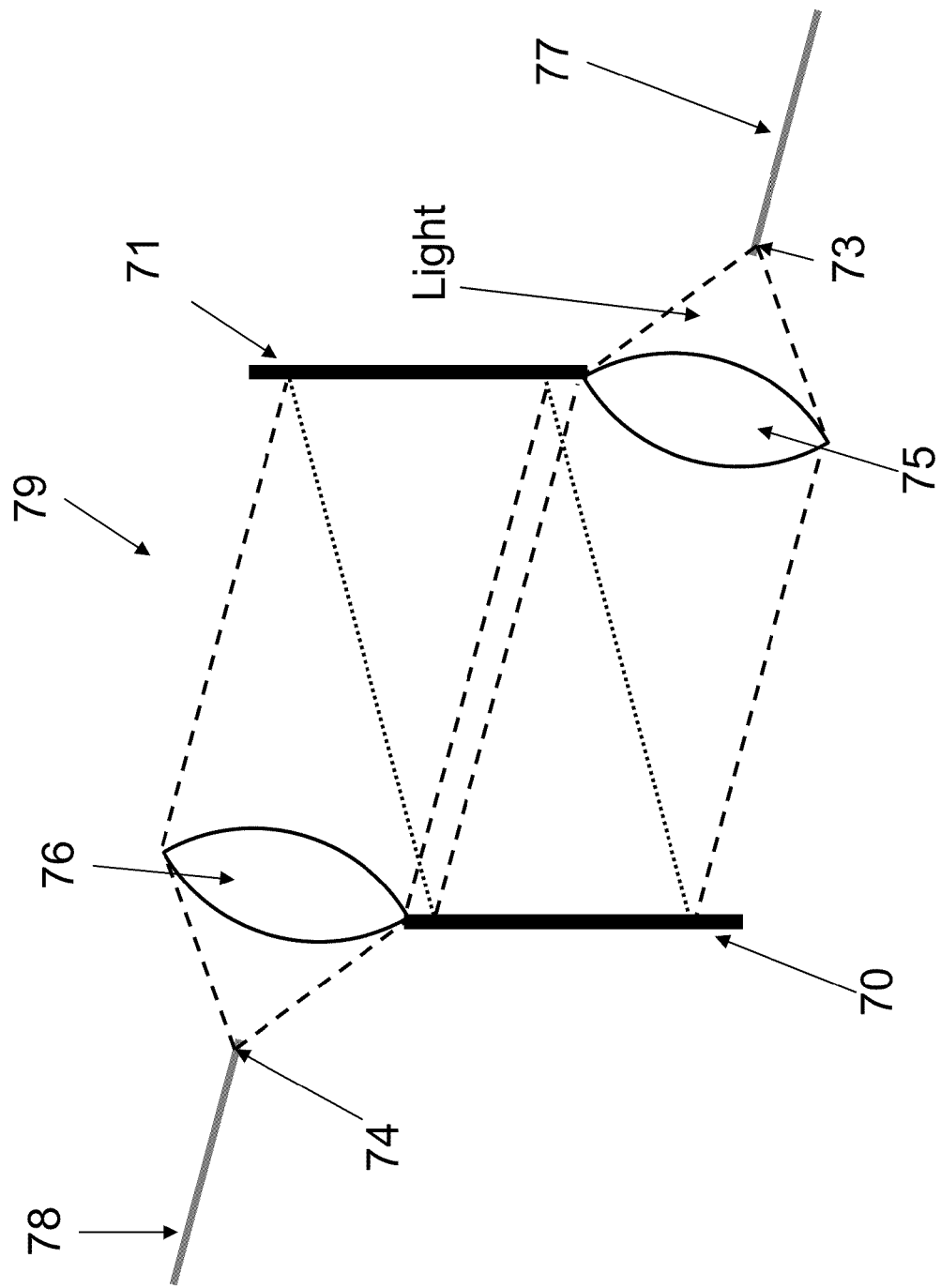
FIG. 8 illustrates a light path between a light emitter and a light receiver in a sensing fluid cavity.

FIG. 8 illustrates a light path between a light emitter 73 and a light receiver 74 in a sensing fluid cavity 79. The borders of the sensing fluid cavity 79 are not shown. It should be understood that the shown mirror/lens arrangement may be used in any of the above described fluid sensing stations including both external fluid sensing stations and end fitting integrated fluid sensing stations. The sensing fluid cavity 79 comprises two lenses 75, 76 and two mirrors 70, 71. It should be understood that the mirror/lens arrangement is only illustrative and that any number of respectively lenses and mirrors could be used to arrange a desired light path between a light emitter and a light receiver.

In use, light is fed to the light emitter 73 via an optical fiber 77. From the light emitter 73 the light path is passing through a first lens 75, which is directing the light with a desired beam width to a first mirror 70 and further to a second mirror 71, from where the light beam is directed to a second lens 76, where the beam width of the light is reduced and the light is directed towards the light receiver 74 from where it can by transmitted to a not shown detector via an optical fiber 78. By using such or similar mirror/lens arrangements the length of the light path in the sensing fluid cavity 79 may be arranged as desired. The lens/mirror arrangement may also be used to filter the light if desired and/or to adjust the light path length in the sensing fluid cavity 79.

Figure 9:
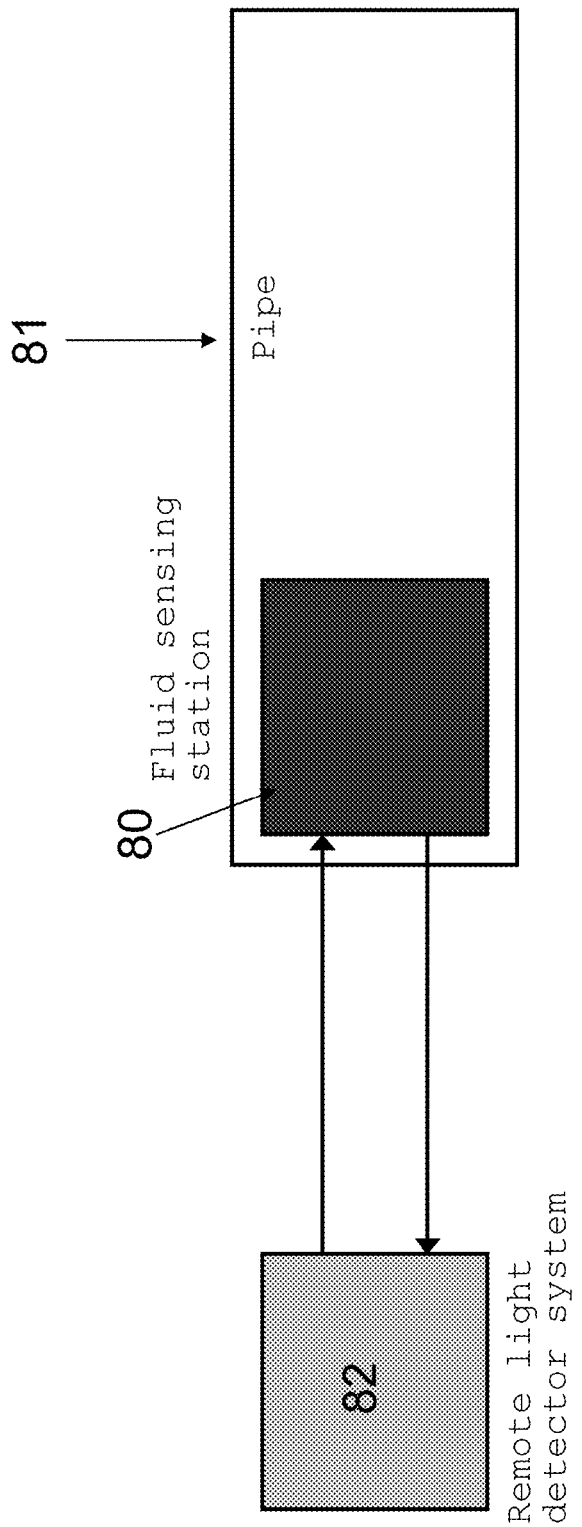
FIG. 9 is a schematic overview of a pipe system of the invention where the fluid sensing station is integrated with the pipe.

FIG. 9 is a schematic overview of a pipe system of the invention. The pipe system comprises a pipe 81, a fluid sensing station 80 and a remote light detector system 82. The fluid sensing station 80 is integrated with the pipe 81. As described and shown above the fluid sensing station 80 may preferably be integrated in the end fitting of the pipe 81. The pipe 81 comprises a not shown flow channel and a not shown annular fluid cavity surrounding the flow channel. The fluid sensing station comprises a not shown sensing fluid cavity which is in fluid communication with the annular fluid cavity. The sensing fluid cavity comprises a not shown light emitter and a not shown light receiver placed at a distance from each other. The light emitter and the light receiver are optically connected to the remote light detector system as indicated by the arrows and as described above.

Figure 10:
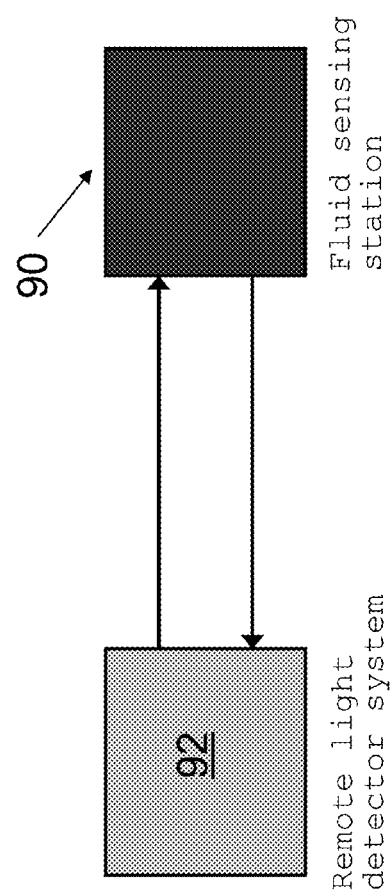
FIG. 10 is a schematic overview of a fluid sensing system of the invention comprising the remote light detector system in one single unit.

FIG. 10 is a schematic overview of a fluid sensing system of the invention. The fluid sensing system comprises a fluid sensing station 90 and a remote light detector system 92. The fluid sensing station 90 comprises a not shown sensing fluid cavity comprising a not shown light emitter and a not shown light receiver placed at a distance from each other and optically connected to each other as described above. The remote light detector system is in one single unit and comprises a not shown light source and a not shown analyzer. The light emitter is optically connected to the light source and the light receiver is optically connected to the analyzer as indicated by the arrows and as described above. The fluid sensing station is adapted to be connected to a pipe with an annular fluid cavity to provide a fluid communication between the annular fluid cavity and the sensing fluid cavity as described above.

Figure 11:
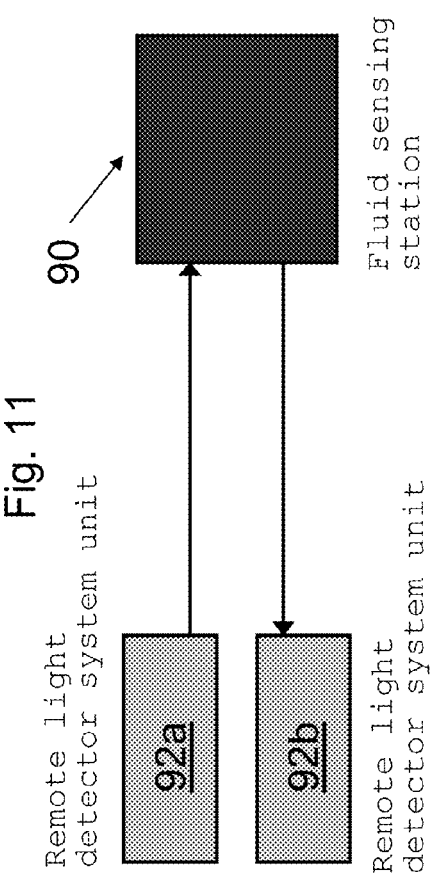
FIG. 11 is a schematic overview of a fluid sensing system of the invention comprising the remote light detector system in two single units.

FIG. 11 is a schematic overview of another fluid sensing system of the invention. The fluid sensing system comprises a fluid sensing station 90 similar to the fluid sensing station described for FIG. 10, and a remote light detector system comprising a first and a second remote light detector system unit 92a, 92b. The first remote light detector system unit 92a comprises a not shown light source arranged to feed light to the light emitter in the fluid sensing station 90 as indicated by the arrows and as described above. The second remote light detector system unit 92b comprises a not shown analyzer arranged to receive light from the light receiver in the fluid sensing station 90 as indicated by the arrows and as described above. The light emitter is optically connected to the light source and the light receiver is optically connected to the analyzer as indicated by the arrows and as described above.

Figure 12:
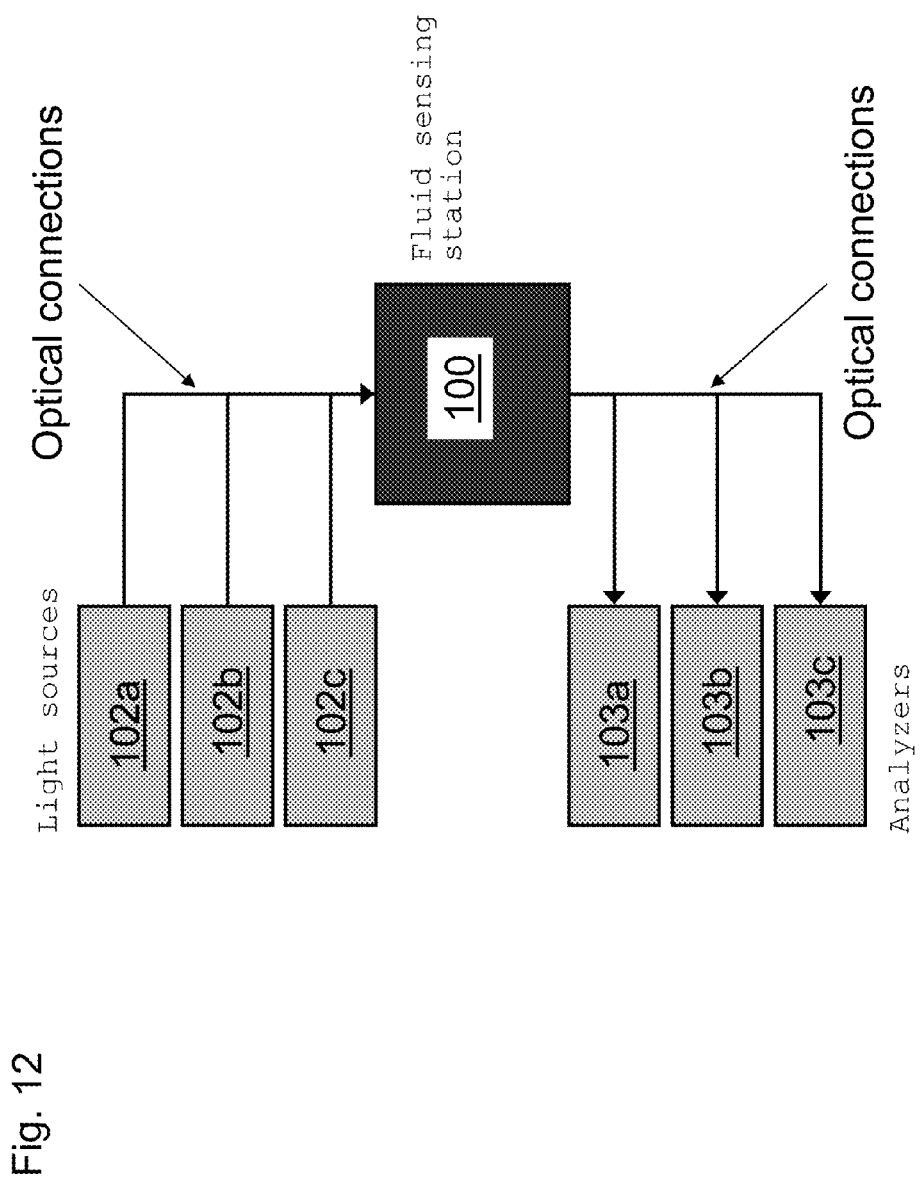
FIG. 12 is a schematic overview of a fluid sensing system of the invention comprising several light sources and several analyzers.

FIG. 12 is a schematic overview of a fluid sensing system of the invention comprising several light sources and several analyzers. The fluid sensing system comprises a fluid sensing station 100 and a remote light detector system comprising a plurality of light sources 102a, 102b, 102c and a plurality of analyzers 103a, 103b, 103c.

The fluid sensing station 100 comprises one or more not shown sensing fluid cavities comprising a plurality of not shown light emitters and a plurality of not shown light receivers placed in pairs (emitter-receiver) at a distance from each other and pair wise optically connected to each other as described above. The plurality of light sources 102a, 102b, 102c and the plurality of analyzers 103a, 103b, 103c may be arranged in one remote light detector system unit or they may be arranged in two or more remote light detector system units. Each light emitter is optically connected to at least one of the light sources 102a, 102b, 102c, and each light receiver is optically connected to at least one of the analyzers 103a, 103b, 103c as indicated by the arrows and as described above. The fluid sensing station 100 is adapted to be connected to a pipe with an annular fluid cavity to provide a fluid communication between the annular fluid cavity and the sensing fluid cavity as described above. The fluid sensing station 100 may for example be provided with a face shaped to fit an outer surface of an end pipe.

Figure 13:
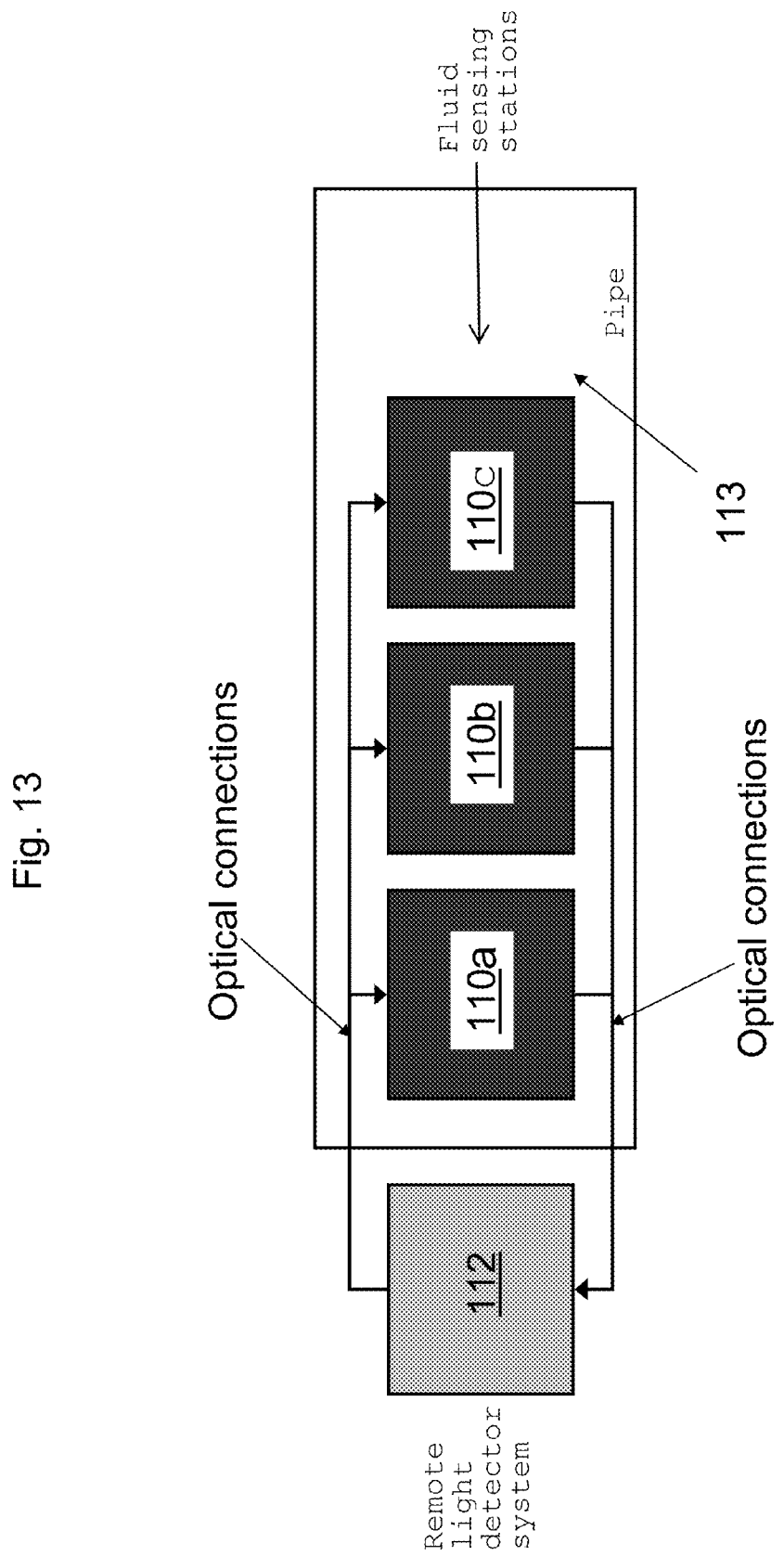
FIG. 13 is a schematic overview of a pipe system of the invention comprising several fluid sensing stations.

FIG. 13 is a schematic overview of another pipe system of the invention The fluid sensing system comprises a plurality of fluid sensing stations 110a, 110b, 110c which each may be similar to the fluid sensing station 90 described for FIG. 10. The fluid sensing system also comprises a remote light detector system 112 which may be similar to the remote light detector system 92 described for FIG. 10.

The light emitters of each of the fluid sensing stations 110a, 110b, 110c are optically connected to the light source of the remote light detector system 112 and the light receivers of each of the fluid sensing stations 110a, 110b, 110c are optically connected to the analyzer of the remote light detector system 112 as indicated by the arrows and as described above. The fluid sensing stations 110a, 110b, 110c are connected to or integrated with one or more pipes 113 as described above.

Figure 14:
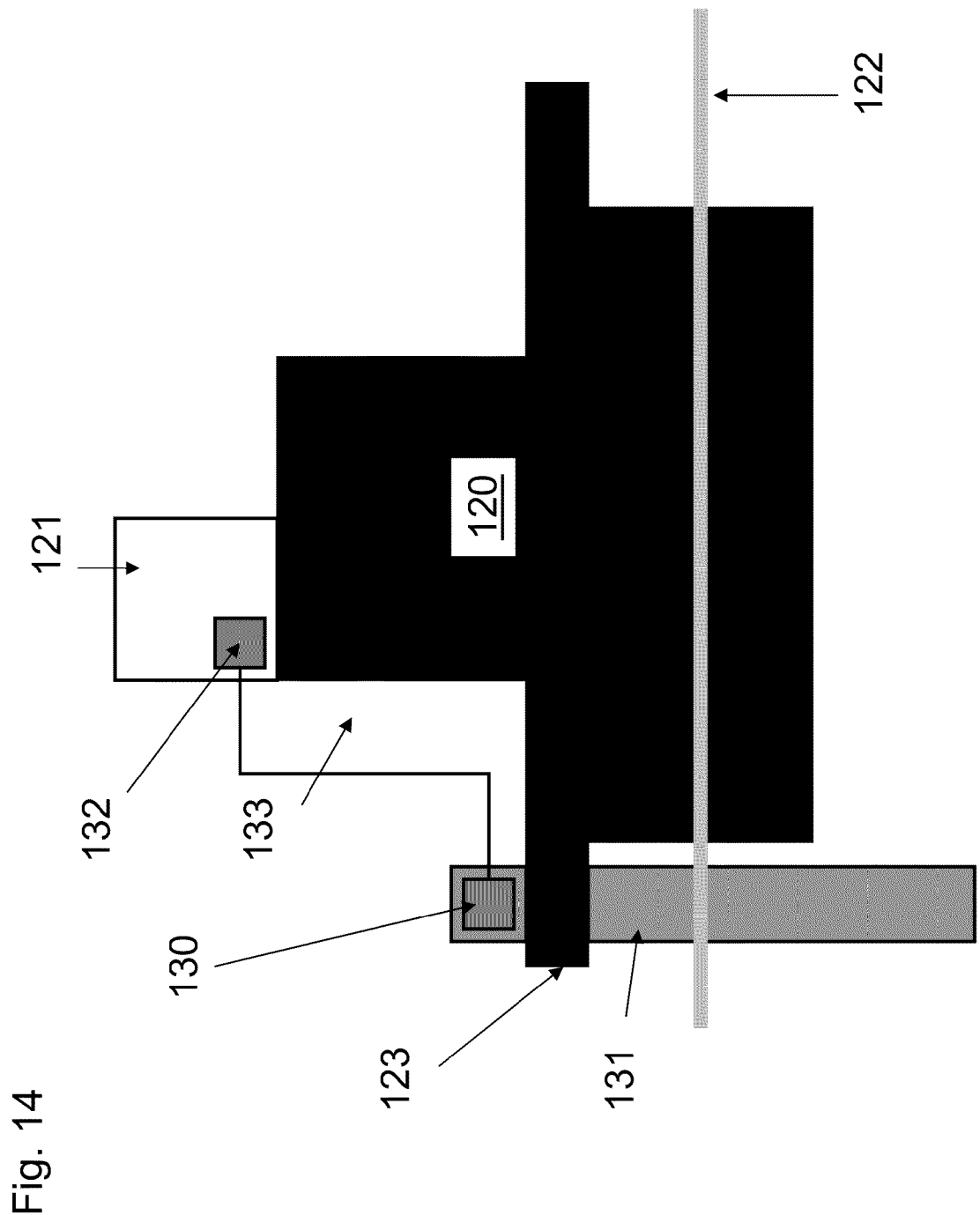
FIG. 14 is a schematic overview of a pipe system of the invention arranged in combination with a production platform.

FIG. 14 is a schematic overview of a pipe system of the invention arranged in combination with a production platform 120. The production platform 120 is an offshore platform as indicated with the waterline 122. The production platform 120 comprises a control room and an anchoring site 123 for securing a pipe. The production platform 120 may preferably also comprise a not shown tank for storing the fluid pumped up from the seabed/underground via the pipe.

The pipe system comprises a pipe 131, a fluid sensing station 130 and a remote light detector system 132. The fluid sensing station 130 is integrated with the pipe 131 or it is fixed to the pipe 131 as described above. The pipe 131 comprises a not shown flow channel and a not shown annular fluid cavity surrounding the flow channel. The fluid sensing station 130 comprises a not shown sensing fluid cavity which is in fluid communication with the annular fluid cavity. The sensing fluid cavity comprises a not shown light emitter and a not shown light receiver placed at a distance from each other. The light emitter and the light receiver are optically connected to the remote light detector system via fibers 133, which should preferably provide a selected—not too small—distance between the pipe 131 and the remote light detector system 132 to thereby ensure a reduced risk of ignition of flammable fluids in and near the pipe. The remote light detector system 132 is located in the control room 121 of the production platform 120.

The invention is defined by the features of the independent claim(s). Preferred embodiments are defined in the dependent claims. Any reference numerals in the claims are intended to be non-limiting for their scope.

Some preferred embodiments have been shown in the foregoing, but it should be stressed that the invention is not limited to these, but may be embodied in other ways within the subject-matter defined in the following claims.

What is claimed is:

1. A pipe system comprising a flexible, unbonded pipe, a fluid sensing station and a remote light detector system, the pipe comprises a flow channel and an annular fluid cavity surrounding the flow channel, the fluid sensing station comprises a sensing fluid cavity which is in fluid communication with the annular fluid cavity, the sensing fluid cavity comprises a light emitter and a light receiver placed at a distance from each other, the light emitter and the light receiver are optically connected to each other and optically connected to the remote light detector system.

2. A pipe system as claimed in claim 1 wherein the pipe is a flexible pipe comprising at least two unbonded layers, the pipe comprises from inside out an internal sheath, one or more armouring layers and an outer sheath, the internal sheath forming a resistance or barrier against the outflow of liquid fluid which is conveyed through the pipe through the flow channel.

3. A pipe system as claimed in claim 1 wherein the pipe comprises an internal sheath and an outer sheath, and the annular fluid cavity is provided between the two sheaths.

4. A pipe system as claimed in claim 1 wherein the annular fluid cavity extends along the length of the pipe in a length of at least 10 m.

5. A pipe system as claimed in claim 1 wherein the remote light detector system comprises a light source optically connected to feed the light emitter in the sensing fluid cavity, the light source is optically connected to the light emitter by an optical fiber.

6. A pipe system as claimed in claim 5 wherein the light source emits light comprising wavelengths which interact with water vapour or one or more of the components selected from oxygen, methane, hydrogen sulphides and carbon dioxides either in gas form or when dissolved in water at least by absorbing or by scattering at least a part of the emitted light.

7. A pipe system as claimed in claim 5 wherein the light source emits light comprising wavelengths in the range $10^{-10}$ to $10^{-2}$ meters.

8. A pipe system as claimed in claim 1 wherein the remote light detector system comprises an analyzer, the analyzer is optically connected to the light receiver in the sensing fluid cavity by an optical fiber.

9. A pipe system as claimed in claim 8, wherein the analyzer is capable of analyzing light comprising wavelengths which interact with or result from an interaction with water vapour or one or more of the components selected from oxygen, methane, hydrogen sulphides and carbon dioxides in gas form or when dissolved in water.

10. A pipe system as claimed in claim 8, wherein the analyzer is capable of analyzing light comprising wavelengths in the range $10^{-10}$ to $10^{-2}$ meters.

11. A pipe system as claimed in claim 1 wherein the remote light detector system comprises a light source and an analyzer, the light source and the analyzer is optically coupled such that the fluid sensing station is capable of comparing the wavelengths or intensities of the emitted light with the corresponding wavelengths or intensities of the received light.

12. A pipe system as claimed in claim 1 wherein the sensing fluid cavity comprises a light emitter and a light receiver placed at a distance from each other, and a gas sensor, the light emitter and the light receiver are optically connected to each other via the gas sensor.

13. A pipe system as claimed in claim 12 wherein a light beam emitted from the light emitter into the gas sensor will be modified in the gas sensor in dependence on the contents of the gas in the sensing fluid cavity.

14. A pipe system as claimed in claim 12 wherein the gas sensor is a photoacoustic spectroscope (PAS).

15. A pipe system as claimed in claim 12 wherein the gas sensor is a Quartz-enhanced photoacoustic spectroscope (QEPAS).

16. A pipe system as claimed in claim 12 wherein the system comprises a light source optically connected to feed the light emitter in the sensing fluid cavity, the light source is selected from a tunable diode laser source, a quantum cascade laser (QCL), an interband cascade laser (ICL) and an optical parametric oscillator (OPO).

17. A pipe system as claimed in claim 1 wherein at least one active element of the remote light detector system is placed at a distance from the fluid sensing station which is at least 2 m, wherein the active elements are selected from the light source and the analyzer.

18. A pipe system as claimed in claim 1 wherein the remote light detector system is placed at a distance from the pipe which is at least 2 m.

19. A pipe system as claimed in claim 1 wherein the remote light detector system is detecting one or more fluid components using at least one of spectroscopy, spectrophotoscopy, Raman scattering, Raman spectroscopy, Resonance Raman spectroscopy, surface enhanced Raman spectroscopy, infrared spectroscopy and ultra-violet spectroscopy.

20. A pipe system as claimed in claim 1 wherein a valve or a filter is arranged in the sensing fluid cavity to control or adjust the pressure in the sensing fluid cavity.

21. A pipe system as claimed in claim 1 wherein the pipe comprises an end fitting, the sensing fluid cavity is provided in the end fitting and is in fluid communication with the annular fluid cavity, and a valve or a filter is arranged between the sensing fluid cavity and the annular fluid cavity.

22. A pipe system as claimed in claim 1 wherein the fluid sensing station is external to the pipe, the pipe comprises an access opening into the annular fluid cavity through which the sensing fluid cavity is in fluid communication with the annular fluid cavity, the access opening is provided with a valve or a filter.

23. A pipe system as claimed in claim 22 wherein the pipe comprises an end fitting, the access opening into the annular fluid cavity is provided via the end fitting.

24. A pipe system as claimed in claim 23 wherein the fluid sensing station is fixed to the end fitting.

25. A pipe system as claimed in claim 23 wherein the fluid sensing station is connected to the end fitting, via a tube fixed to respectively the fluid sensing station and the end fitting.

26. A pipe system as claimed in claim 1 wherein the sensing fluid cavity comprises the light emitter optically connected to the light receiver, wherein the optical connection comprises an exposure length where the light providing the optical connection is exposed to a fluid in the sensing fluid cavity, the exposure length is between 1 mm and 500 cm.

27. A pipe system as claimed in claim 26 wherein the exposure length is adjustable.

28. A pipe system as claimed in claim 1 wherein the pipe is an offshore pipe.

29. A method of determining a fluid component in an annular fluid cavity of a pipe comprising the use of a pipe system as claimed in claim 1, the method comprises emitting light from said light emitter and receiving emitted light by said light receiver and transmitting the received light to the remote light detector system for determining the fluid component.

30. A method as claimed in claim 29, wherein the determination comprises performing a qualitative determination of the presence of one or more components, selected from oxygen, methane, hydrogen sulphides and carbon dioxides in gas form or when dissolved in water.

31. A method as claimed in claim 29, wherein the determination comprises performing a quantitative determination of the amount of one or more components, selected from oxygen, methane, hydrogen sulphides and carbon dioxides in gas form or when dissolved in water.

32. A method as claimed in claim 29, wherein the system is connected to an alarm, the method comprises activating said alarm if the determined results deviate from a set point or deviate significantly from previous determinations.

33. A pipe system as claimed in claim 3 wherein the pipe comprises one or more intermediate sheaths, and at least two of the sheaths of the pipe are barrier sheaths that form a barrier against fluid, and the annular fluid cavity is provided between the two barrier sheaths.

34. A fluid sensing system for sensing a fluid in an annulus cavity of a pipe, the fluid sensing system comprises a fluid sensing station and a remote light detector system, the fluid sensing station comprises a sensing fluid cavity comprising a light emitter and a light receiver placed at a distance from each other and optically connected to each other, the remote light detector system comprises a light source and an analyzer, the light emitter is optically connected to the light source, the light receiver is optically connected to the analyzer, the fluid sensing station is arranged to be connected to a pipe with an annular fluid cavity to provide a fluid communication between the annular fluid cavity and the sensing fluid cavity.

35. A fluid sensing system as claimed in claim 34 wherein the light source is adapted to emit light comprising wavelengths which interact with water vapour or one or more of the components selected from oxygen, methane, hydrogen sulphides and carbon dioxides either in gas form or when dissolved in water at least by absorbing or scattering at least a part of the emitted light.

36. A fluid sensing system as claimed in claim 34 wherein the sensing fluid cavity comprises a light emitter and a light receiver placed at a distance from each other, and a gas sensor, the light emitter and the light receiver is optically connected to each other via the gas sensor.

37. A fluid sensing system as claimed in claim 36 wherein the gas sensor is a photoacoustic spectroscope (PAS).

38. A fluid sensing system as claimed in claim 36 wherein the system comprises a light source for optically connected to feed the light emitter in the sensing fluid cavity, the light source is selected from a tunable diode laser source, a quantum cascade laser (QCL), an interband cascade lasers (ICL) and an optical parametric oscillator (OPO).

39. A fluid sensing system as claimed in claim 34 wherein the sensing fluid cavity comprises a gas sensor in the form of a photoacoustic spectroscope (PAS), the remote light detector system is detecting one or more fluid components by analyzing the signal received from the light receiver.

40. A fluid sensing system as claimed in claim 34 wherein the remote light detector system comprises a light source and an analyzer, the light source and the analyzer is optically coupled such that the fluid sensing station is capable of comparing the wavelengths or intensities of the emitted light with the corresponding wavelengths or intensities of the received light.

41. A fluid sensing system as claimed in claim 34 wherein the fluid sensing system is adapted to be connected to a pipe comprising an access opening into an annular fluid cavity, the sensing fluid cavity is adapted to be in fluid communication with the annular fluid cavity through the access opening.

* * * * *

UNITED STATES PATENT AND TRADEMARK OFFICE
CERTIFICATE OF CORRECTION

PATENT NO. : 8,593,636 B2
APPLICATION NO. : 12/919070
DATED : November 26, 2013
INVENTOR(S) : Mikael Kristiansen and Nicky Weppenaar It is certified that error appears in the above-identified patent and that said Letters Patent is hereby corrected as shown below:

In the Specification, column 5, line 67, please replace "$10^{-19}$" with - $10^{-10}$ -

Signed and Sealed this
Twenty-fifth Day of February, 2014

Michelle K. Lee
*Deputy Director of the United States Patent and Trademark Office*

UNITED STATES PATENT AND TRADEMARK OFFICE
CERTIFICATE OF CORRECTION

PATENT NO.        : 8,593,636 B2                                                              Page 1 of 1
APPLICATION NO. : 12/919070
DATED             : November 26, 2013
INVENTOR(S)       : Kristiansen et al.

It is certified that error appears in the above-identified patent and that said Letters Patent is hereby corrected as shown below:

On the Title Page:

The first or sole Notice should read --

Subject to any disclaimer, the term of this patent is extended or adjusted under 35 U.S.C. 154(b) by 606 days.

Signed and Sealed this
Twenty-second Day of September, 2015

Michelle K. Lee
*Director of the United States Patent and Trademark Office*